(12) United States Patent
Purcell et al.

(10) Patent No.: US 11,191,630 B2
(45) Date of Patent: Dec. 7, 2021

(54) SYSTEMS AND METHODS FOR PROTECTING THE CEREBRAL VASCULATURE

(71) Applicant: Claret Medical, Inc., Santa Rosa, CA (US)

(72) Inventors: Cameron Paul Purcell, Santa Rosa, CA (US); Antony J. Fields, Santa Rosa, CA (US); Whittaker Ian Hamill, Petaluma, CA (US); Daniel Wayne Fifer, Windsor, CA (US)

(73) Assignee: Claret Medical, Inc., Santa Rosa, CA (US)

( * ) Notice: Subject to any disclaimer, the term of this patent is extended or adjusted under 35 U.S.C. 154(b) by 383 days.

(21) Appl. No.: 16/173,604

(22) Filed: Oct. 29, 2018

(65) Prior Publication Data
US 2019/0125513 A1 May 2, 2019

Related U.S. Application Data

(60) Provisional application No. 62/577,870, filed on Oct. 27, 2017.

(51) Int. Cl.
*A61F 2/01* (2006.01)
*A61M 25/01* (2006.01)

(52) U.S. Cl.
CPC .............. *A61F 2/012* (2020.05); *A61F 2/013* (2013.01); *A61M 25/0147* (2013.01);
(Continued)

(58) Field of Classification Search
CPC .. A61F 2/01; A61F 2/012; A61F 2/013; A61F 2/011; A61F 2/95; A61F 2002/016;
(Continued)

(56) References Cited

U.S. PATENT DOCUMENTS

| | | |
|---|---|---|
| 3,472,230 A | 10/1969 | Fogarty |
| 4,619,246 A | 10/1986 | Molgaard-Nielsen et al. |

(Continued)

FOREIGN PATENT DOCUMENTS

| | | |
|---|---|---|
| DE | 10049812 A1 | 4/2002 |
| EP | 1400257 A2 | 3/2004 |

(Continued)

OTHER PUBLICATIONS

International Search Report and Written Opinion dated Jan. 29, 2019 for International Application No. PCT/US2018/057978.
(Continued)

*Primary Examiner* — Kathleen S Holwerda
*Assistant Examiner* — Lauren Dubose
(74) *Attorney, Agent, or Firm* — Seager, Tufte & Wickhem, LLP

(57) ABSTRACT

Vascular filters and deflectors and methods for filtering bodily fluids. A blood filtering assembly can capture embolic material dislodged or generated during an endovascular procedure to inhibit or prevent the material from entering the cerebral vasculature. A blood deflecting assembly can deflect embolic material dislodged or generated during an endovascular procedure to inhibit or prevent the material from entering the cerebral vasculature.

14 Claims, 21 Drawing Sheets

(52) U.S. Cl.
CPC ......... *A61F 2/011* (2020.05); *A61F 2002/016* (2013.01); *A61F 2210/0014* (2013.01); *A61F 2230/0067* (2013.01); *A61F 2230/0093* (2013.01)

(58) Field of Classification Search
CPC ...... A61F 2230/0067; A61F 2230/0093; A61F 2210/0014; A61M 25/0147; A61M 25/0052; A61M 2025/1052; A61B 17/12109
USPC .................................................. 606/200, 192
See application file for complete search history.

(56) References Cited

U.S. PATENT DOCUMENTS

| | | |
|---|---|---|
| 4,630,609 A | 12/1986 | Chin |
| 4,650,466 A | 3/1987 | Luther |
| 4,706,671 A | 11/1987 | Weinrib |
| 4,723,549 A | 2/1988 | Wholey et al. |
| 4,873,978 A | 10/1989 | Ginsburg |
| 5,108,419 A | 4/1992 | Reger |
| 5,192,286 A | 3/1993 | Phan et al. |
| 5,200,248 A | 4/1993 | Thompson et al. |
| 5,329,923 A | 7/1994 | Lundquist |
| 5,348,545 A | 9/1994 | Shani et al. |
| 5,381,782 A | 1/1995 | DeLaRama et al. |
| 5,395,327 A | 3/1995 | Lundquist et al. |
| 5,613,980 A | 3/1997 | Chauhan |
| 5,624,430 A | 4/1997 | Eton et al. |
| 5,662,671 A | 9/1997 | Barbut et al. |
| 5,680,873 A | 10/1997 | Berg et al. |
| 5,707,389 A | 1/1998 | Louw et al. |
| 5,766,151 A | 6/1998 | Valley et al. |
| 5,779,716 A | 7/1998 | Cano et al. |
| 5,814,064 A | 9/1998 | Daniel et al. |
| 5,827,324 A | 10/1998 | Cassell |
| 5,833,650 A | 11/1998 | Imran |
| 5,848,964 A | 12/1998 | Samuels |
| 5,897,529 A | 4/1999 | Ponzi |
| 5,897,819 A | 4/1999 | Miyata et al. |
| 5,910,154 A | 6/1999 | Tsugita et al. |
| 5,910,364 A | 6/1999 | Miyata et al. |
| 5,911,734 A | 6/1999 | Tsugita et al. |
| 5,935,139 A | 8/1999 | Bates |
| 5,980,555 A | 11/1999 | Barbut et al. |
| 5,989,281 A | 11/1999 | Barbut et al. |
| 5,993,469 A | 11/1999 | McKenzie et al. |
| 6,001,118 A | 12/1999 | Daniel et al. |
| 6,010,522 A | 1/2000 | Barbut et al. |
| 6,027,520 A | 2/2000 | Tsugita et al. |
| 6,042,598 A | 3/2000 | Tsugita et al. |
| 6,045,547 A | 4/2000 | Ren et al. |
| 6,051,014 A | 4/2000 | Jang |
| 6,080,140 A | 6/2000 | Swaminathan et al. |
| 6,083,239 A | 7/2000 | Addis |
| 6,096,053 A | 8/2000 | Bates |
| 6,099,534 A | 8/2000 | Bates et al. |
| 6,120,494 A | 9/2000 | Jonkman |
| 6,126,673 A | 10/2000 | Kim et al. |
| 6,129,739 A | 10/2000 | Khosravi |
| 6,142,987 A | 11/2000 | Tsugita |
| 6,146,396 A | 11/2000 | Konya |
| 6,152,946 A | 11/2000 | Broome et al. |
| 6,171,328 B1 | 1/2001 | Addis |
| 6,179,851 B1 | 1/2001 | Barbut et al. |
| 6,179,861 B1 | 1/2001 | Khosravi et al. |
| 6,203,561 B1 | 3/2001 | Ramee et al. |
| 6,214,026 B1 | 4/2001 | Lepak et al. |
| 6,235,045 B1 | 5/2001 | Barbut et al. |
| 6,245,087 B1 | 6/2001 | Addis |
| 6,245,088 B1 | 6/2001 | Lowery |
| 6,245,089 B1 | 6/2001 | Daniel et al. |
| 6,264,663 B1 | 7/2001 | Cano |
| 6,270,513 B1 | 8/2001 | Tsugita et al. |
| 6,277,138 B1 | 8/2001 | Levinson et al. |
| 6,287,321 B1 | 9/2001 | Jang |
| 6,290,710 B1 | 9/2001 | Cryer et al. |
| 6,309,399 B1 | 10/2001 | Barbut et al. |
| 6,325,815 B1 | 12/2001 | Kusleika et al. |
| 6,336,934 B1 | 1/2002 | Gilson et al. |
| 6,336,116 B1 | 2/2002 | Brooks et al. |
| 6,361,545 B1 | 3/2002 | Macoviak et al. |
| 6,364,900 B1 | 4/2002 | Heuser |
| 6,371,970 B1 | 4/2002 | Khosravi |
| 6,371,971 B1 | 4/2002 | Tsugita et al. |
| 6,375,628 B1 | 4/2002 | Zadno-Azizi et al. |
| 6,383,174 B1 | 5/2002 | Eder |
| 6,383,205 B1 | 5/2002 | Samson |
| 6,440,120 B1 | 8/2002 | Maahs |
| 6,454,799 B1 | 9/2002 | Schreck |
| 6,485,502 B2 | 11/2002 | Don Michael |
| 6,499,487 B1 | 12/2002 | McKenzie et al. |
| 6,517,559 B1 | 2/2003 | O'Connell |
| 6,530,939 B1 | 3/2003 | Hopkins et al. |
| 6,537,297 B2 | 3/2003 | Tsugita et al. |
| 6,544,279 B1 | 4/2003 | Hopkins et al. |
| 6,558,356 B2 | 5/2003 | Barbut |
| 6,589,263 B1 | 7/2003 | Hopkins et al. |
| 6,595,983 B2 | 7/2003 | Voda |
| 6,605,102 B1 | 8/2003 | Mazzocchi |
| 6,616,679 B1 | 9/2003 | Khosravi et al. |
| 6,620,148 B1 | 9/2003 | Tsugita |
| 6,620,182 B1 | 9/2003 | Khosravi et al. |
| 6,648,837 B2 | 11/2003 | Kato et al. |
| 6,663,652 B2 | 12/2003 | Daniel et al. |
| 6,676,682 B1 | 1/2004 | Tsugita et al. |
| 6,712,834 B2 | 3/2004 | Yassour et al. |
| 6,712,835 B2 | 3/2004 | Mazzocchi |
| 6,719,717 B1 | 4/2004 | Johnson et al. |
| 6,726,621 B2 | 4/2004 | Suon et al. |
| 6,726,651 B1 | 4/2004 | Robinson et al. |
| 6,726,701 B2 | 4/2004 | Gilson |
| 6,740,061 B1 | 5/2004 | Oslund |
| 6,817,999 B2 | 11/2004 | Berube et al. |
| 6,830,579 B2 | 12/2004 | Barbut |
| 6,843,798 B2 | 1/2005 | Kusleika et al. |
| 6,872,216 B2 | 3/2005 | Daniel |
| 6,881,194 B2 | 4/2005 | Miyata et al. |
| 6,887,258 B2 | 5/2005 | Denison et al. |
| 6,905,490 B2 | 6/2005 | Parodi |
| 6,907,298 B2 | 6/2005 | Smits et al. |
| 6,958,074 B2 | 10/2005 | Russell |
| 6,969,396 B2 | 11/2005 | Krolik et al. |
| 7,011,094 B2 | 3/2006 | Rapacki et al. |
| 7,048,752 B2 | 5/2006 | Mazzocchi |
| 7,094,249 B1 | 8/2006 | Broome |
| 7,115,134 B2 | 10/2006 | Chambers |
| 7,160,255 B2 | 1/2007 | Saadat |
| 7,169,161 B2 | 1/2007 | Bonnette et al. |
| 7,169,165 B2 | 1/2007 | Belef et al. |
| 7,182,757 B2 | 2/2007 | Miyata et al. |
| 7,214,237 B2 | 5/2007 | Don Michael |
| 7,278,974 B2 | 10/2007 | Kato et al. |
| 7,303,575 B2 | 12/2007 | Ogle |
| 7,306,618 B2 | 12/2007 | Demond et al. |
| 7,313,445 B2 | 12/2007 | McVenes et al. |
| 7,323,001 B2 | 1/2008 | Clubb et al. |
| 7,329,278 B2 | 2/2008 | Seguin et al. |
| 7,399,308 B2 | 7/2008 | Borillo et al. |
| 7,410,491 B2 | 8/2008 | Hopkins |
| 7,493,154 B2 | 2/2009 | Bonner et al. |
| 7,559,925 B2 | 7/2009 | Goldfarb et al. |
| 7,572,272 B2 | 8/2009 | Denison et al. |
| 7,621,904 B2 | 11/2009 | McFerran et al. |
| 7,722,634 B2 | 5/2010 | Panetta et al. |
| 7,766,961 B2 | 8/2010 | Patel et al. |
| 7,922,732 B2 | 3/2011 | Mazzocchi et al. |
| 7,918,859 B2 | 4/2011 | Katoh et al. |
| 7,976,562 B2 | 7/2011 | Bressler et al. |
| 7,998,104 B2 | 8/2011 | Chang |
| 8,002,790 B2 | 8/2011 | Brady et al. |
| 8,021,351 B2 | 9/2011 | Boldenow et al. |
| 8,052,713 B2 | 11/2011 | Khosravi et al. |

(56) References Cited

U.S. PATENT DOCUMENTS

| | | |
|---|---|---|
| 8,092,483 B2 | 1/2012 | Galdonik et al. |
| 8,206,412 B2 | 6/2012 | Galdonik et al. |
| 8,372,108 B2 | 2/2013 | Lashinski |
| 8,382,788 B2 | 2/2013 | Galdonik |
| 8,460,335 B2 | 6/2013 | Carpenter |
| 8,518,073 B2 | 8/2013 | Lashinski |
| 8,753,370 B2 | 6/2014 | Lashinski |
| 8,876,796 B2 | 11/2014 | Fifer et al. |
| 8,974,489 B2 | 3/2015 | Lashinski |
| 9,017,364 B2 | 4/2015 | Fifer et al. |
| 9,055,997 B2 | 6/2015 | Fifer et al. |
| 9,259,306 B2 | 2/2016 | Fifer et al. |
| 9,326,843 B2 | 5/2016 | Lee et al. |
| 9,345,565 B2 | 5/2016 | Fifer et al. |
| 9,480,548 B2 | 11/2016 | Carpenter |
| 9,492,264 B2 | 11/2016 | Fifer et al. |
| 9,566,144 B2 * | 2/2017 | Purcell ............... A61F 2/013 |
| 9,636,205 B2 | 5/2017 | Lee et al. |
| 9,943,395 B2 | 4/2018 | Fifer et al. |
| 9,980,805 B2 | 5/2018 | Fifer |
| 2001/0041858 A1 | 11/2001 | Ray et al. |
| 2002/0022858 A1 | 2/2002 | Demond et al. |
| 2002/0026145 A1 | 2/2002 | Bagaoisan et al. |
| 2002/0055767 A1 | 5/2002 | Forde et al. |
| 2002/0068015 A1 | 6/2002 | Polaschegg et al. |
| 2002/0077596 A1 | 6/2002 | McKenzie et al. |
| 2002/0095170 A1 | 7/2002 | Krolik et al. |
| 2002/0095172 A1 | 7/2002 | Mazzocchi et al. |
| 2002/0123761 A1 | 9/2002 | Barbut et al. |
| 2002/0161394 A1 | 10/2002 | Macoviak et al. |
| 2002/0165571 A1 | 11/2002 | Herbert et al. |
| 2002/0165573 A1 | 11/2002 | Barbut |
| 2003/0100919 A1 | 5/2003 | Hopkins et al. |
| 2003/0130684 A1 | 7/2003 | Brady et al. |
| 2003/0144686 A1 | 7/2003 | Martinez et al. |
| 2003/0171770 A1 | 9/2003 | Kusleika et al. |
| 2003/0199960 A1 | 10/2003 | Paskar |
| 2004/0002730 A1 | 1/2004 | Denison et al. |
| 2004/0006370 A1 | 1/2004 | Tsugita |
| 2004/0044350 A1 | 3/2004 | Martin et al. |
| 2004/0044360 A1 | 3/2004 | Lowe |
| 2004/0064092 A1 | 4/2004 | Tsugita et al. |
| 2004/0093015 A1 | 5/2004 | Ogle |
| 2004/0167565 A1 | 8/2004 | Beulke et al. |
| 2004/0193206 A1 | 9/2004 | Gerberding |
| 2004/0215167 A1 | 10/2004 | Belson |
| 2004/0215230 A1 | 10/2004 | Frazier |
| 2004/0220611 A1 | 11/2004 | Ogle |
| 2004/0225321 A1 | 11/2004 | Krolik et al. |
| 2004/0230220 A1 | 11/2004 | Osborne |
| 2004/0243175 A1 | 12/2004 | Don Michael |
| 2004/0254601 A1 | 12/2004 | Eskuri |
| 2004/0254602 A1 | 12/2004 | Lehe et al. |
| 2005/0010285 A1 | 1/2005 | Lambrecht et al. |
| 2005/0065397 A1 | 3/2005 | Saadat et al. |
| 2005/0080356 A1 | 4/2005 | Dapolito et al. |
| 2005/0085847 A1 | 4/2005 | Galdonik et al. |
| 2005/0101987 A1 | 5/2005 | Salahieh |
| 2005/0131449 A1 | 6/2005 | Salahieh et al. |
| 2005/0137696 A1 | 6/2005 | Salahieh |
| 2005/0177132 A1 | 8/2005 | Lentz et al. |
| 2005/0209631 A1 | 9/2005 | Galdonik et al. |
| 2005/0277976 A1 | 12/2005 | Galdonik et al. |
| 2006/0015136 A1 | 1/2006 | Besselink |
| 2006/0015138 A1 | 1/2006 | Gertner |
| 2006/0030877 A1 | 2/2006 | Martinez et al. |
| 2006/0041188 A1 | 2/2006 | Dirusso et al. |
| 2006/0047301 A1 | 3/2006 | Ogle |
| 2006/0089618 A1 | 4/2006 | McFerran et al. |
| 2006/0089666 A1 | 4/2006 | Linder et al. |
| 2006/0100658 A1 | 5/2006 | Obana et al. |
| 2006/0100662 A1 | 5/2006 | Daniel et al. |
| 2006/0129180 A1 | 6/2006 | Tsugita et al. |
| 2006/0135961 A1 | 6/2006 | Rosenman et al. |
| 2006/0136043 A1 | 6/2006 | Cully et al. |
| 2006/0149350 A1 | 7/2006 | Patel et al. |
| 2006/0161241 A1 * | 7/2006 | Barbut ............... A61F 2/856 623/1.15 |
| 2006/0200047 A1 | 9/2006 | Galdonik et al. |
| 2006/0200191 A1 | 9/2006 | Zadno-Azizi |
| 2006/0259066 A1 | 11/2006 | Euteneuer |
| 2007/0005131 A1 | 1/2007 | Taylor |
| 2007/0043259 A1 | 2/2007 | Jaffe et al. |
| 2007/0060944 A1 | 3/2007 | Boldenow et al. |
| 2007/0088244 A1 | 4/2007 | Miller et al. |
| 2007/0088383 A1 | 4/2007 | Pal et al. |
| 2007/0173878 A1 | 7/2007 | Heuser |
| 2007/0191880 A1 | 8/2007 | Cartier et al. |
| 2007/0208302 A1 | 9/2007 | Webster et al. |
| 2007/0244504 A1 | 10/2007 | Keegan et al. |
| 2008/0004687 A1 | 1/2008 | Barbut |
| 2008/0033467 A1 | 2/2008 | Miyamoto et al. |
| 2008/0058860 A1 | 3/2008 | Demond et al. |
| 2008/0065145 A1 | 3/2008 | Carpenter |
| 2008/0065147 A1 | 3/2008 | Mazzocchi et al. |
| 2008/0086110 A1 | 4/2008 | Galdonik et al. |
| 2008/0109088 A1 | 5/2008 | Galdonik et al. |
| 2008/0125848 A1 | 5/2008 | Kusleika et al. |
| 2008/0154153 A1 | 6/2008 | Heuser |
| 2008/0172066 A9 | 6/2008 | Galdonik et al. |
| 2008/0188884 A1 | 8/2008 | Gilson et al. |
| 2008/0234722 A1 | 9/2008 | Bonnette et al. |
| 2008/0262442 A1 | 10/2008 | Carlin et al. |
| 2008/0300462 A1 | 12/2008 | Intoccia et al. |
| 2009/0024072 A1 | 1/2009 | Criado et al. |
| 2009/0024153 A1 | 1/2009 | Don Michael |
| 2009/0069840 A1 | 3/2009 | Hallisey |
| 2009/0198269 A1 | 8/2009 | Hannes et al. |
| 2009/0203962 A1 | 8/2009 | Miller et al. |
| 2009/0254172 A1 | 10/2009 | Grewe et al. |
| 2009/0287187 A1 | 11/2009 | Legaspi et al. |
| 2009/0326575 A1 | 12/2009 | Galdonik et al. |
| 2010/0004633 A1 | 1/2010 | Rothe et al. |
| 2010/0010476 A1 | 1/2010 | Galdonik et al. |
| 2010/0063537 A1 | 3/2010 | Ren et al. |
| 2010/0106182 A1 | 4/2010 | Patel et al. |
| 2010/0179583 A1 | 7/2010 | Carpenter et al. |
| 2010/0179584 A1 | 7/2010 | Carpenter et al. |
| 2010/0179585 A1 | 7/2010 | Carpenter et al. |
| 2010/0179647 A1 | 7/2010 | Carpenter et al. |
| 2010/0185216 A1 | 7/2010 | Garrison et al. |
| 2010/0191276 A1 | 7/2010 | Lashinski |
| 2010/0211095 A1 | 8/2010 | Carpenter |
| 2010/0228280 A1 | 9/2010 | Groothius et al. |
| 2010/0312268 A1 | 12/2010 | Belson |
| 2010/0324589 A1 | 12/2010 | Carpenter et al. |
| 2011/0066221 A1 | 3/2011 | White et al. |
| 2012/0046739 A1 | 2/2012 | von Oepen et al. |
| 2012/0095500 A1 | 4/2012 | Heuser |
| 2012/0172920 A1 * | 7/2012 | Fifer ............... A61F 2/013 606/200 |
| 2012/0203265 A1 | 8/2012 | Heuser |
| 2013/0123835 A1 | 5/2013 | Anderson et al. |
| 2013/0131714 A1 | 5/2013 | Wang et al. |
| 2013/0231694 A1 | 9/2013 | Lashinski |
| 2014/0052170 A1 | 2/2014 | Heuser et al. |
| 2014/0094843 A1 | 4/2014 | Heuser |
| 2014/0100597 A1 | 4/2014 | Wang et al. |
| 2014/0249567 A1 | 9/2014 | Adams et al. |
| 2014/0282379 A1 | 9/2014 | Bijani et al. |
| 2015/0039016 A1 | 2/2015 | Naor et al. |
| 2015/0073533 A1 | 3/2015 | Kassab et al. |
| 2015/0230910 A1 | 8/2015 | Lashinski et al. |
| 2015/0335416 A1 | 11/2015 | Fifer et al. |
| 2016/0058541 A1 | 3/2016 | Schotzko et al. |
| 2016/0066880 A1 * | 3/2016 | Stigall ............... A61B 8/5207 600/424 |
| 2016/0262864 A1 | 9/2016 | Von Mangoldt et al. |
| 2016/0310255 A1 | 10/2016 | Purcell et al. |
| 2017/0042658 A1 | 2/2017 | Lee et al. |
| 2017/0112609 A1 | 4/2017 | Purcell et al. |
| 2017/0181834 A1 | 6/2017 | Fifer et al. |

(56) References Cited

U.S. PATENT DOCUMENTS

| | | |
|---|---|---|
| 2017/0202657 A1 | 7/2017 | Lee et al. |
| 2018/0177582 A1 | 6/2018 | Lashinski |
| 2018/0235742 A1 | 8/2018 | Fields et al. |

FOREIGN PATENT DOCUMENTS

| | | |
|---|---|---|
| EP | 1253871 B1 | 2/2007 |
| EP | 2303384 A2 | 4/2011 |
| EP | 2391303 A2 | 12/2011 |
| EP | 2480165 A2 | 8/2012 |
| EP | 2658476 A1 | 11/2013 |
| EP | 2387427 B1 | 8/2014 |
| EP | 2859864 A1 | 4/2015 |
| JP | 2003505216 A | 2/2003 |
| JP | 2003526451 A | 9/2003 |
| JP | 2003290231 A | 10/2003 |
| JP | 3535098 B2 | 6/2004 |
| JP | 2006500187 A | 1/2006 |
| JP | 2008511401 A | 4/2008 |
| JP | 2008511401 A1 | 4/2008 |
| JP | 2008515463 A | 5/2008 |
| JP | 2008515463 A1 | 5/2008 |
| JP | 2011525405 A | 9/2011 |
| WO | 9923976 A1 | 5/1999 |
| WO | 0021604 A1 | 4/2000 |
| WO | 0108743 A1 | 2/2001 |
| WO | 0167989 A2 | 9/2001 |
| WO | 2004026175 A1 | 4/2004 |
| WO | 2005118050 A2 | 12/2005 |
| WO | 2006026371 A1 | 3/2006 |
| WO | 2006076505 A2 | 7/2006 |
| WO | 2008033845 A2 | 3/2008 |
| WO | 2008100790 A2 | 8/2008 |
| WO | 2008113857 A2 | 9/2008 |
| WO | 2009032834 A1 | 3/2009 |
| WO | 2010008451 A2 | 1/2010 |
| WO | 2010081025 A1 | 7/2010 |
| WO | 2010083527 A2 | 7/2010 |
| WO | 2010088520 A2 | 8/2010 |
| WO | 2011034718 A2 | 3/2011 |
| WO | 2011017103 A2 | 10/2011 |
| WO | 2012092377 A1 | 7/2012 |
| WO | 2018156655 A1 | 8/2018 |

OTHER PUBLICATIONS

Internet Archive Wayback Machine; Fiber Innovative Technology: FIT Capabilities; downloaded from http://web.archive.org/web/20010217040848/http://www.fitfibers.com/capabilities.htm (Archived Feb. 17, 2001; printed on Dec. 12, 2016).

Internet Archive Wayback Machine; Fiber Innovative Technology: 4DG Fibers; downloaded from http://web.archive.org/web/20011030070010/http://fitfibers.com/4DG_Fibers.htm (Archived Oct. 30, 2001; printed on Dec. 12, 2016).

Internet Archive Wayback Machine; Fiber Innovative Technology: FIT Products; downloaded from http://web.archive.org/web/20010408003529/http://www.fitfibers.com/product.htm (Archived Apr. 8, 2001; printed on Dec. 12, 2016).

* cited by examiner

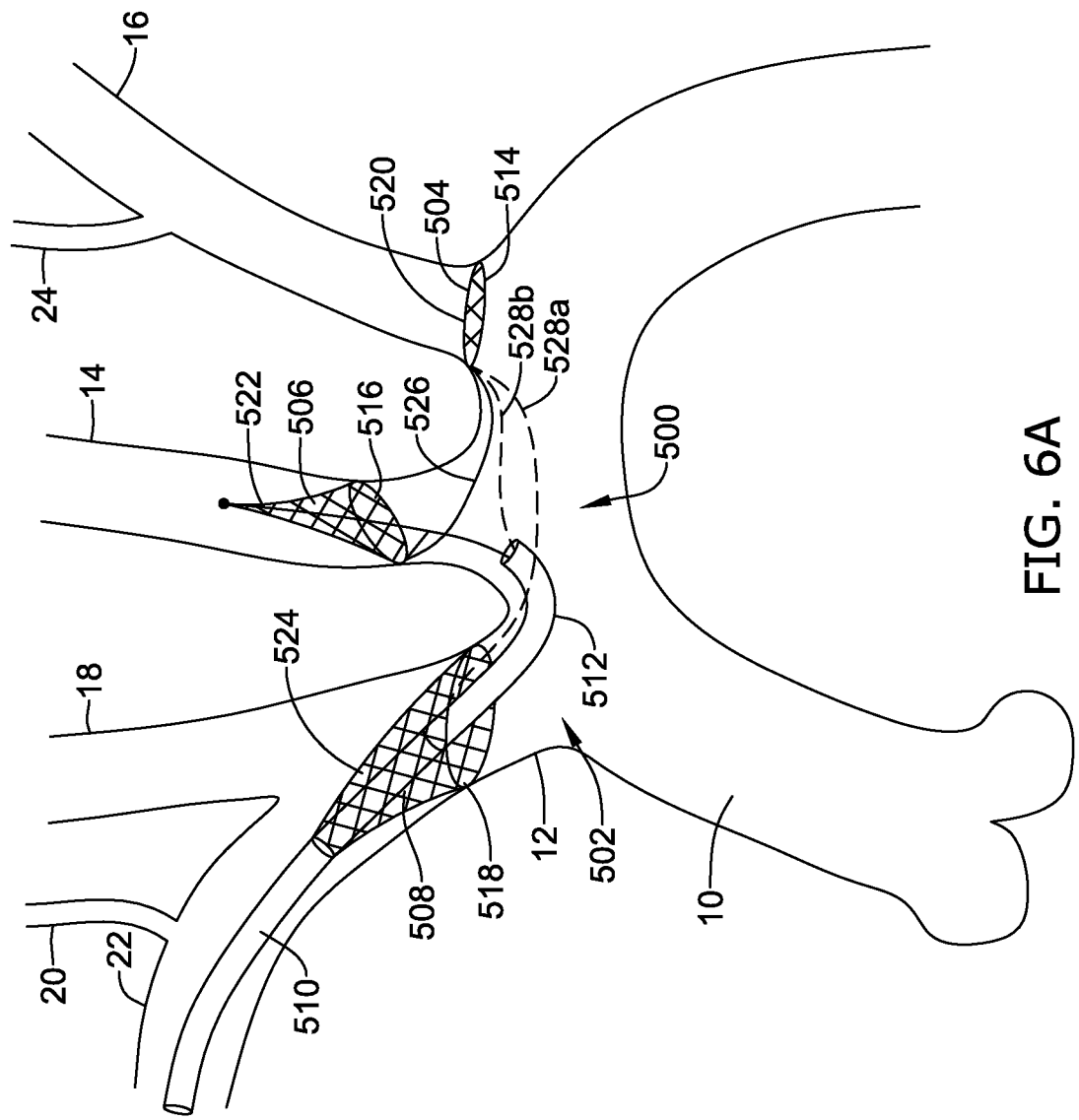

SYSTEMS AND METHODS FOR PROTECTING THE CEREBRAL VASCULATURE

CROSS-REFERENCE TO RELATED APPLICATIONS

This application claims the benefit of priority under 35 U.S.C. § 119 to U.S. Provisional Application Ser. No. 62/577,870, filed Oct. 27, 2017, the entirety of which is incorporated herein by reference.

TECHNICAL FIELD

In general, the present disclosure relates to medical devices for filtering blood. And, more particularly, in certain embodiments, to a method and a system of filters and deflectors for protecting the cerebral arteries from emboli, debris and the like dislodged during an endovascular or cardiac procedure.

BACKGROUND

There are four arteries that carry oxygenated blood to the brain, i.e., the right and left vertebral arteries, and the right and left common carotid arteries. Various procedures conducted on the human body, e.g., transcatheter aortic valve replacement (TAVR), aortic valve valvuloplasty, carotid artery stenting, closure of the left atrial appendage, mitral valve annuloplasty, repair or replacement, can cause and/or dislodge materials (whether native or foreign), these dislodged bodies can travel into one or more of the cerebral arteries resulting in, inter alia, stroke.

There exist devices for protecting one or more cerebral arteries by either collecting (filters) or deflecting (deflectors) debris. Single filters, such as those used during a carotid artery stenting are one such device.

Applicants have previously patented a dual filter embolic protection system that protects the right vertebral, and right and left common carotid arteries, see e.g., U.S. Pat. No. 9,492,264, the entirety of which is incorporated herein. Other attempts at deflecting debris from entering one or more cerebral arteries using a deflector placed in the aorta or aortic arch have also been disclosed. Of the known medical devices, delivery systems, and methods, each has certain advantages and disadvantages. There is an ongoing need to provide alternative medical devices and methods as well as alternative methods for manufacturing and using medical devices.

SUMMARY

Certain aspects of the present disclosure address debris, tissue, etc., that can be dislodged during an endovascular procedure, this debris can travel toward, into and embolize within the cerebral vasculature leading to stroke or ischemia in an artery occluded, partially or totally, by the clot. For example, during a transcatheter aortic valve replacement (TAVR), stenotic material around the valve can be dislodged during implantation of the artificial valve. Moreover, atheroma along and within the aorta and aortic arch can be dislodged as the TAVR catheter is advanced toward the diseased aortic valve and subsequently withdrawn after implantation is completed. In addition, pieces of the catheter itself can be stripped away during delivery and implantation. These various forms of vascular debris, whether native or foreign, can then travel into one or more cerebral arteries, embolize and cause a stroke, strokes or neurocognitive deficits, for example.

Certain aspects of the present disclosure are intended to address these potentially devastating cerebral events by providing a delivery system comprised of filters and/or deflectors and/or combinations thereof, to intercept this debris before it can enter any of the cerebral arteries.

Certain aspects of the present disclosure, and its various embodiments, can provide a compound system of filters and/or deflectors for collecting (and/or deflecting) debris in a manner such that all four cerebral arteries are protected.

Vascular filters and deflectors and methods for filtering bodily fluids are disclosed herein. A blood filtering assembly can capture embolic material dislodged or generated during an endovascular procedure to inhibit or prevent the material from entering the cerebral vasculature. A blood deflecting assembly can deflect embolic material dislodged or generated during an endovascular procedure to inhibit or prevent the material from entering the cerebral vasculature.

In a first example a method of inhibiting embolic material from entering cerebral vasculature may comprise positioning a guidewire through a right subclavian artery and into a left subclavian artery and tracking a distal portion of a first protection device over the guidewire. The distal portion of the first protection device may comprise an outer sheath, a first self-expanding filter assembly radially within the outer sheath. The method may further comprise at least one of proximally retracting the outer sheath and distally advancing the self-expanding filter assembly to deploy the first self-expanding filter assembly from the outer sheath in the left subclavian artery upstream of the left vertebral artery. After deploying the self-expanding filter assembly, the method may further comprise withdrawing the outer sheath from the right subclavian artery and withdrawing the guidewire into an innominate artery and tracking a distal portion of a second protection device over the guidewire. The distal portion of the second protection device may comprise a proximal sheath, a proximal self-expanding filter assembly radially within the proximal sheath, a distal sheath, and a distal self-expanding filter assembly radially within the distal sheath The method may further comprise at least one of proximally retracting the proximal sheath and distally advancing the proximal self-expanding filter assembly to deploy the proximal self-expanding filter assembly from the proximal sheath in the innominate artery, steering the distal sheath into a left common carotid artery, at least one of proximally retracting the distal sheath and distally advancing the distal self-expanding filter assembly to deploy the distal self-expanding filter assembly from the distal sheath in the left common carotid artery, and after deploying the proximal and distal self-expanding filter assemblies, withdrawing the proximal and distal sheaths.

Alternatively or additionally to any of the examples above, in another example, the first protection device and the second protection device may be inserted into a right radial artery or a right brachial artery through a same incision.

Alternatively or additionally to any of the examples above, in another example, the method may further comprise performing an endovascular procedure, the deployed first, proximal, and distal filter assemblies inhibiting embolic material from entering cerebral vasculature through the left vertebral artery, a right common carotid artery, a right vertebral artery and the left common carotid artery during the endovascular procedure.

Alternatively or additionally to any of the examples above, in another example, the method may further comprise after performing the endovascular procedure, withdrawing the first, proximal, and distal filter assemblies.

Alternatively or additionally to any of the examples above, in another example, the first protection device may further comprise an inner member radially inward of the outer sheath.

Alternatively or additionally to any of the examples above, in another example, the method may further comprise measuring an arterial pressure using one of the first and second protection devices.

Alternatively or additionally to any of the examples above, in another example, the first protection device may further comprise a filter wire coupled to a proximal end of the first self-expanding filter and extending distally therefrom.

Alternatively or additionally to any of the examples above, in another example, an entirety of a length of the second protection device may be tracked over the filter wire.

Alternatively or additionally to any of the examples above, in another example, less than an entirety of a length of the second protection device may be tracked over the filter wire.

Alternatively or additionally to any of the examples above, in another example, the second protection device may further comprise a rapid exchange port.

In another example, a method of inhibiting embolic material from entering cerebral vasculature may comprise positioning a guidewire through a right subclavian artery and into a left subclavian artery and tracking a distal portion of a first protection device over the guidewire. The distal portion of the first protection device may comprise an outer sheath, an inner member radially inward of the outer sheath, the inner member comprising a guidewire lumen, and a first self-expanding filter assembly radially between the outer sheath and the inner member, the first self-expanding filter assembly having an opening facing a proximal end of the outer sheath. The method may further comprise at least one of proximally retracting the outer sheath and distally advancing the self-expanding filter assembly to deploy the first self-expanding filter assembly from the outer sheath in the left subclavian artery upstream of the left vertebral artery, after deploying the self-expanding filter assembly, withdrawing the outer sheath from the right subclavian artery and withdrawing the guidewire into an innominate artery, and tracking a distal portion of a second protection device over the guidewire. The distal portion of the second protection device may comprise a proximal sheath, a proximal self-expanding filter assembly radially within the proximal sheath, an articulatable distal sheath, and a distal self-expanding filter assembly radially within the distal sheath. The method may further comprise at least one of proximally retracting the proximal sheath and distally advancing the proximal self-expanding filter assembly to deploy the proximal self-expanding filter assembly from the proximal sheath in the innominate artery, steering the distal sheath into a left common carotid artery, at least one of proximally retracting the distal sheath and distally advancing the distal self-expanding filter assembly to deploy the distal self-expanding filter assembly from the distal sheath in the left common carotid artery, and after deploying the proximal and distal self-expanding filter assemblies, withdrawing the proximal and distal sheaths.

Alternatively or additionally to any of the examples above, in another example, the first protection device and the second protection device may be inserted into a right radial artery or a right brachial artery through a same incision.

Alternatively or additionally to any of the examples above, in another example, the method may further comprise performing an endovascular procedure, the deployed first, proximal, and distal filter assemblies inhibiting embolic material from entering cerebral vasculature through the left vertebral artery, a right common carotid artery, a right vertebral artery and the left common carotid artery during the endovascular procedure.

Alternatively or additionally to any of the examples above, in another example, the method may further comprise after performing the endovascular procedure, withdrawing the first, proximal, and distal filter assemblies.

In another example, a method of inhibiting embolic material from entering cerebral vasculature may comprise positioning a guidewire in a first artery, tracking a distal portion of a first protection device over the guidewire. The distal portion of the first protection device may comprise a proximal sheath, a proximal self-expanding filter assembly radially within the proximal sheath, a distal sheath, a distal self-expanding filter assembly radially within the distal sheath, and an intermediate self-expanding filter assembly radially within the distal sheath. The method may further comprise at least one of proximally retracting the proximal sheath and distally advancing the proximal self-expanding filter assembly to deploy the proximal self-expanding filter assembly from the proximal sheath in the first artery, steering the distal sheath into a second artery, at least one of proximally retracting the distal sheath and distally advancing the distal self-expanding filter assembly to deploy the distal self-expanding filter assembly from the distal sheath in the second artery, steering the distal sheath into a third artery, at least one of proximally retracting the distal sheath and distally advancing the intermediate self-expanding filter assembly to deploy the distal self-expanding filter assembly from the distal sheath in the third artery, and after deploying the proximal, distal, and intermediate self-expanding filter assemblies, withdrawing the proximal and distal sheaths.

Alternatively or additionally to any of the examples above, in another example, the first protection device may be inserted into a right radial artery or a right brachial artery.

Alternatively or additionally to any of the examples above, in another example, the method may further comprise performing an endovascular procedure, the deployed proximal, intermediate, and distal self-expanding filter assemblies inhibiting embolic material from entering cerebral vasculature through the left vertebral artery, a right common carotid artery, a right vertebral artery and the left common carotid artery during the endovascular procedure.

Alternatively or additionally to any of the examples above, in another example, the method may further comprise after performing the endovascular procedure, withdrawing the proximal, intermediate, and distal filter assemblies.

Alternatively or additionally to any of the examples above, in another example, the first protection device may further comprise a tether extending between the distal self-expanding filter assembly and the intermediate self-expanding filter assembly.

Alternatively or additionally to any of the examples above, in another example, the tether may have a preformed shape configured to guide the intermediate filter assembly towards the third artery.

In another example, an embolic protection system for isolating the cerebral vasculature may comprise a first protection device having a proximal portion configured to remain outside the body and a distal portion and a second protection device having a proximal portion configured to remain outside the body and a distal portion. The distal portion of the first protection device may comprise an outer sheath and a first self-expanding filter assembly radially within the outer sheath. The distal portion of the second protection device may comprise a proximal sheath, a proximal self-expanding filter assembly radially within the proximal sheath, a distal sheath, and a distal self-expanding filter assembly radially within the distal sheath.

Alternatively or additionally to any of the examples above, in another example, the first self-expanding filter assembly may include a proximally facing opening.

Alternatively or additionally to any of the examples above, in another example, the proximal self-expanding filter assembly may include a distally facing opening.

Alternatively or additionally to any of the examples above, in another example, the distal self-expanding filter assembly may include a proximally facing opening.

Alternatively or additionally to any of the examples above, in another example, the first protection device may further comprise a filter wire coupled to a proximal end of the first self-expanding filter and extending distally therefrom.

Alternatively or additionally to any of the examples above, in another example, the second protection device may further comprise a lumen configured to receive the filter wire of the first protection device.

Alternatively or additionally to any of the examples above, in another example, the lumen may extend over less than an entire length of the second protection device.

Alternatively or additionally to any of the examples above, in another example, the lumen may be in communication with a rapid exchange port proximally spaced from a distal end of the distal sheath.

Alternatively or additionally to any of the examples above, in another example, the lumen may extend an entirety of a length of the second protection device.

Alternatively or additionally to any of the examples above, in another example, the first protection device may further comprise an inner member radially inward of the outer sheath.

Alternatively or additionally to any of the examples above, in another example, the inner member may comprise a guidewire lumen.

Alternatively or additionally to any of the examples above, in another example, at least one of the first or second protection devices may be connected to an arterial pressure monitoring device.

Alternatively or additionally to any of the examples above, in another example, the distal sheath may be articulatable.

Alternatively or additionally to any of the examples above, in another example, each of the first self-expanding filter, the proximal self-expanding filter, and the distal self-expanding filter may be configured to be individually deployed.

Alternatively or additionally to any of the examples above, in another example, the embolic protection system may further comprise a first handle assembly coupled to the proximal portion of the first embolic protection device and a second handle assembly coupled to the proximal portion of the second embolic protection device.

The above summary of exemplary embodiments is not intended to describe each disclosed embodiment or every implementation of the present disclosure.

BRIEF DESCRIPTION OF THE DRAWINGS

The invention may be more completely understood in consideration of the following detailed description of various embodiments in connection with the accompanying drawings, in which:

FIGS. 6A and 6B illustrate embodiments of deploying two filters and a deflector.

Figure 1A:
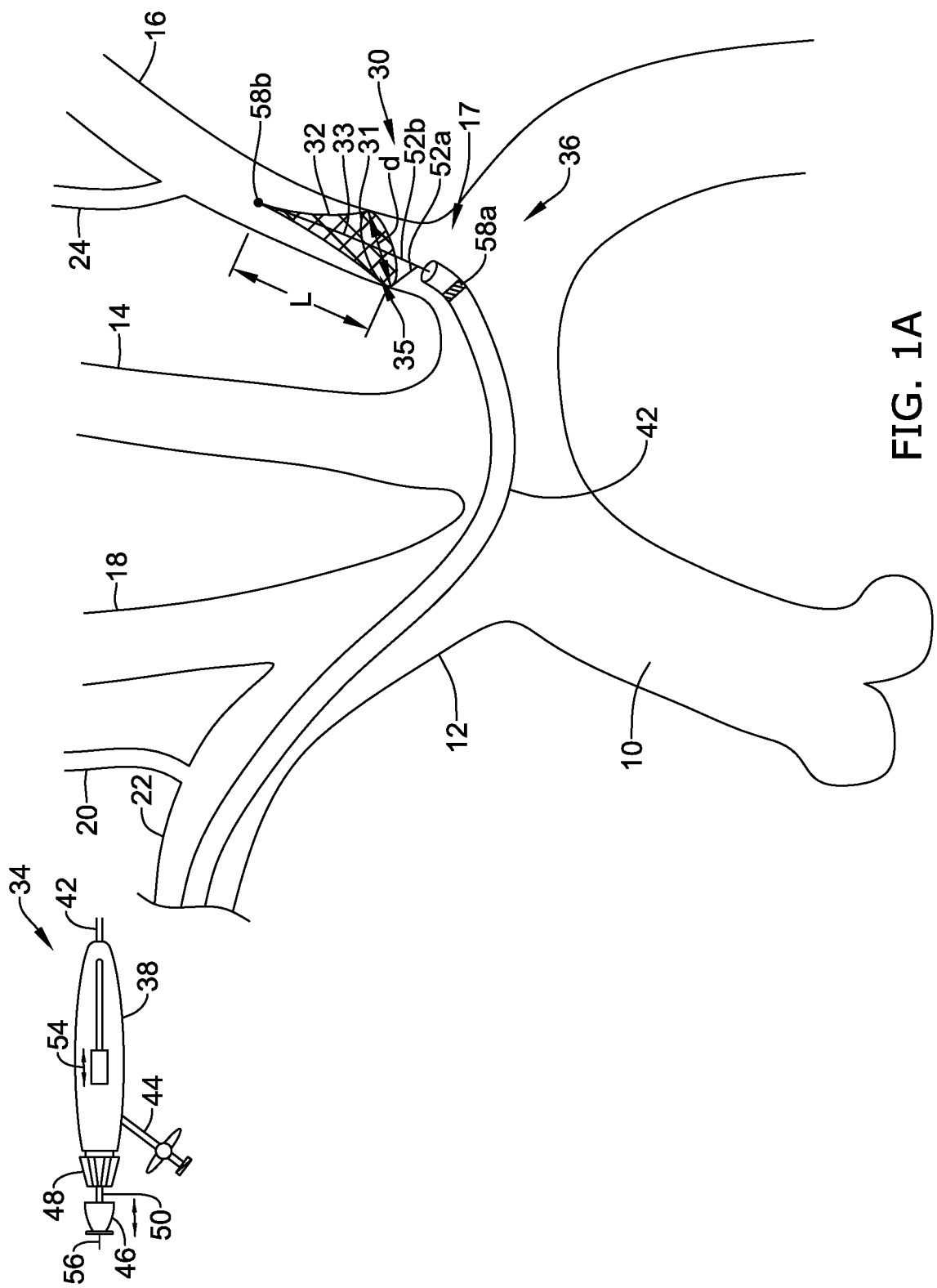
FIGS. 1A and 1B illustrate a first embodiment for deploying three filters to protect the cerebral vascular architecture.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

The currently marketed Sentinel system made by Claret Medical and embodiments of which are described in U.S. Pat. No. 9,492,264 mentioned above has two filters, a first which protects the right brachiocephalic artery, from which the right vertebral and right common carotid arteries typically originate, and a second filter in the left common carotid artery. In a typical patient, the left vertebral which provides approximately seven percent of the perfusion to the brain is left unprotected.

One disclosed solution to protecting the left vertebral is the use of a second device intended to be placed in the left arm, e.g. through the left radial artery, with a filter placed in the left subclavian from which the left vertebral typically originates. Embodiments of such a solution can be found in U.S. Pat. No. 9,566,144, the entirety of which is hereby incorporated by reference herein and included as part of this Specification in an Appendix (labeled Appendix B) filed with this patent application.

While procedurally compatible, it may be preferred to achieve protection of all cerebral vessels from one access point. Deflector concepts which reside in the arch have been previously disclosed, and these devices can have a single access point of either the right arm, left arm or femoral artery. While deflector concepts which reside in the arch are technically feasible, they may result in substantial interference with the therapy (e.g. TAVR) or procedure, or may not be sufficiently compatible with the breadth of sizes and configurations of aortic arches to provide complete protection of the brain.

The present application discloses several single-access multi-vessel embodiments that can provide full cerebral protection with minimal arch interference.

The disclosure generally relates to devices and methods for filtering fluids and/or deflecting debris contained within fluids, including body fluids such as blood. A filtering or deflecting device can be positioned in an artery before and/or during an endovascular procedure (e.g., transcatheter aortic valve implantation (TAVI) or replacement (TAVR), transcatheter mitral valve implantation (TAMI) or replacement (TAMR), surgical aortic valve replacement (SAVR), other surgical valve repair, implantation, or replacement, cardiac ablation (e.g., ablation of the pulmonary vein to treat atrial fibrillation) using a variety of energy modalities (e.g., radio frequency (RF), energy, cryo, microwave, ultrasound), cardiac bypass surgery (e.g., open-heart, percutaneous), transthoracic graft placement around the aortic arch, valvuloplasty, etc.) to inhibit or prevent embolic material such as debris, emboli, thrombi, etc. resulting from entering the cerebral vasculature.

The devices may be used to trap and/or deflect particles in other blood vessels within a subject, and they can also be used outside of the vasculature. The devices described herein are generally adapted to be delivered percutaneously to a target location within a subject, but can be delivered in any suitable way and need not be limited to minimally-invasive procedures.

FIG. 1A is a schematic view of an aortic arch 10 including a first protection device 30. The aortic arch 10 is upstream of the left and right coronary arteries (not explicitly shown). The aortic arch 10 typically includes three great branch arteries: the brachiocephalic artery or innominate artery 12, the left common carotid artery 14, and the left subclavian artery 16. The innominate artery 12 branches to the right carotid artery 18, then the right vertebral artery 20, and thereafter is the right subclavian artery 22. The right subclavian artery 22 supplies blood to, and may be directly accessed from (termed right radial access), the right arm.

The left subclavian artery 16 branches to the left vertebral artery 24, usually in the shoulder area. The left subclavian artery 16 supplies blood to, and may be directly accessed from (termed left radial axis), the left arm. Four of the arteries illustrated in FIG. 1A supply blood to the cerebral vasculature: (1) the left carotid artery 14 (about 40% of cerebral blood supply); (2) the right carotid artery 18 (about 40% of cerebral blood supply); (3) the right vertebral artery 20 (about 10% of cerebral blood supply); and (4) the left vertebral artery 24 (about 10% of cerebral blood supply).

It may be desirable to filter blood flow to all four arteries 14, 18, 20, 24 supplying blood to the brain and/or deflect particulates from entering the arteries 14, 18, 20, 24 supplying the brain. It may also be desirable to limit the number of incision sites or cuts required to deploy the system(s). FIG. 1A illustrates a first step in deploying a multi-filter system using a right radial access incision. The first filter 32 may be deployed in the left subclavian artery 16 upstream of the left vertebral artery 24.

The protection device, or filter system, 30 comprises a proximal portion 34 and a distal portion 36. The proximal portion 34 is configured to be held and manipulated by a user such as a surgeon. The distal portion 36 is configured to be positioned at a target location such as the left subclavian artery 16 or the left vertebral artery 24. When the distal portion 36 is configured to be positioned at the left subclavian artery 16, the location may be upstream of the left vertebral artery 24 such that the blood is filtered prior to entering the left vertebral artery 24.

The proximal portion 34 may include a handle 38, a control 40 such as a slider, an outer sheath 42, a port 44, optionally an inner member translation control 46 such as a knob, and optionally a hemostasis valve control 48 such as a knob. The proximal portion 34 may also comprises an inner member 50 radially inward of the outer sheath 42. While not explicitly shown, the proximal portion 34 may also comprise a filter wire 52b radially inward of the outer sheath 42 (and sometimes radially outward of the inner member 50). Some illustrative filter wires are described in commonly assigned U.S. Pat. No. 9,566,144, the entirety of which is hereby incorporated by reference. The filter wire 52b may be coupled to the filter assembly 32 in the distal portion 36. The outer sheath 42 may have a diameter between about 4 French (Fr) (approximately 1.33 millimeters (mm)) and about 6 Fr (approximately 2 mm) (e.g., about 5 Fr (approximately 1.67 mm)).

The protection device 30 may further include a guidewire 56 disposed within a lumen of the inner member 50. The outer sheath 42 may comprise an atraumatic distal tip. Other features of the protection device 30 and other protection devices described herein may be flexible and/or atraumatic. The outer sheath 42 may comprise a curvature, for example based on an intended placement location (e.g., the left subclavian artery and/or the left vertebral artery).

The slider 40 can be used to translate the outer sheath 42 and/or a filter assembly 32 (e.g., coupled to a filter wire 52b). For example, the slider 40 may proximally retract the outer sheath 42, the slider 40 may distally advance the filter assembly 32 out of the outer sheath 42, or the slider 40 may proximally retract the outer sheath 42 and distally advance the filter assembly 32 (e.g., simultaneously or serially), which can allow the filter assembly 32 to radially expand. The slider 40 may also be configured to have an opposite translation effect, which can allow the filter assembly 32 to be radially collapsed (e.g., due to compression by the outer sheath 42) as the filter assembly 32 is drawn into the outer sheath 42. Other deployment systems are also possible, for example comprising gears or other features such as helical tracks (e.g., configured to compensate for any differential lengthening due to foreshortening of the filter assembly 32, configured to convert rotational motion into longitudinal motion), a mechanical element, a pneumatic element, a hydraulic element, etc. for opening and/or closing the filter assembly 32.

The port 44 is in fluid communication with the inner member 50 (e.g., via a Y-shaped connector in the handle 38). The port 44 can be used to flush the device (e.g., with saline) before, during, and/or after use, for example to remove air. The port 44 can additionally, or alternatively, be used to monitor blood pressure at the target location, for example by connecting an arterial pressure monitoring device in fluid communication with a lumen of the outer sheath 42. The port 44 can be also or alternatively be used to inject contrast agent, dye, thrombolytic agents such as tissue plasminogen activator (t-PA), etc. The slider 40 may be independent of the inner member 50 such that the inner member 50 is longitudinally movable independent of the filter assembly 32 and the outer sheath 42. The inner member translation control 46 can be used to longitudinally translate the inner member 50, for example before, after, and/or during deployment of the filter assembly 32. The inner member translation control 46 may comprise a slider in the housing 38 (e.g., separate from the slider 40).

The rotatable hemostasis valve control 48 can be used to reduce or minimize fluid loss through the protection device 30 during use. For example, a proximal portion and/or intermediate region of the protection device may be positioned in the right subclavian artery 22 and the direction of blood flow with respect to the device 30 will be distal to proximal, so blood may be otherwise inclined to follow the pressure drop out of the device 30. The hemostasis valve control 48 is illustrated as being rotatable, but other arrangements are also possible (e.g., longitudinally displaceable). The hemostasis valve control 48 may be configured to fix relative positions of the outer sheath 42 and the filter assembly 32, for example as described with respect to the hemostasis valve in U.S. Pat. No. 8,876,796. The hemostasis valve 48 may comprise, for example, an elastomeric seal and HV nut.

The distal portion 36 may include the outer sheath 42, a filter assembly 32 radially inward of the outer sheath 42 in a delivery configuration (not explicitly shown), and optionally the inner member 50. The filter assembly 32 may be radially between the outer sheath 42 and the inner member 50 (e.g., radially inward of the outer sheath 42 and the inner member 50 radially inward of the filter assembly 32) in a delivery state or shape or position.

The filter assembly 32 may include a support element or frame 31 and a filter element 33. The frame 31 may generally provide expansion support to the filter element 33 in the expanded state. In the expanded state, the filter element 33 is configured to filter fluid (e.g., blood) flowing through the filter element 33 and to inhibit or prevent particles (e.g., embolic material) from flowing through the filter element 33 by capturing the particles in the filter element 33.

The frame 31 is configured to engage or appose the inner walls of a lumen (e.g., blood vessel) in which the frame assembly 32 is expanded. The frame 31 may comprise or be constructed of, for example, nickel titanium (e.g., nitinol), nickel titanium niobium, chromium cobalt (e.g., MP35N, 35NLT), copper aluminum nickel, iron manganese silicon, silver cadmium, gold cadmium, copper tin, copper zinc, copper zinc silicon, copper zinc aluminum, copper zinc tin, iron platinum, manganese copper, platinum alloys, cobalt nickel aluminum, cobalt nickel gallium, nickel iron gallium, titanium palladium, nickel manganese gallium, stainless steel, combinations thereof, and the like. The frame 31 may comprise a wire (e.g., having a round (e.g., circular, elliptical) or polygonal (e.g., square, rectangular) cross-section). For example, in some embodiments, the frame 31 comprises a straight piece of nitinol wire shape set into a circular or oblong hoop or hoop with one or two straight legs running longitudinally along or at an angle to a longitudinal axis of the frame assembly 32. At least one of the straight legs may be coupled to a filter wire 52a or a strut 52a. The straight legs may be on a long side of the filter assembly 32 and/or on a short side of the filter assembly 32. The frame 31 may form a shape of an opening 35 of the filter assembly 32. The opening 35 may be circular, elliptical, or any shape that can appropriately appose sidewalls of a vessel such as the left subclavian artery or the left vertebral artery. The filter assembly 32 may have a generally proximally-facing opening 35. In other embodiments, the opening 35 may be distally facing. The orientation of the opening 35 may vary depending on where the access incision is located.

The frame 31 may include a radiopaque marker such as a small coil wrapped around or coupled to the hoop to aid in visualization under fluoroscopy. In some embodiments, the frame may not comprise a shape other than a hoop, for example a spiral. In some embodiments, the filter assembly 32 may not include or be substantially free of a frame.

In some embodiments, the frame 31 and the filter element 33 form an oblique truncated cone having a non-uniform or unequal length around and along the length of the filter assembly 32. In such a configuration, along the lines of a windsock, the filter assembly 32 has a larger opening 35 (upstream) diameter and a reduced ending (downstream) diameter.

The filter element 33 may include pores configured to allow blood to flow through the filter element 33, but that are small enough to inhibit prevent particles such as embolic material from passing through the filter element 33. The filter element 33 may comprise a filter membrane such as a polymer (e.g., polyurethane, polytetrafluoroethylene (PTFE)) film mounted to the frame 32. The filter element may have a thickness between about 0.0001 inches and about 0.03 inches (e.g., no more than about 0.0001 inches, about 0.001 inches, about 0.005 inches, about 0.01 inches, about 0.015 inches, about 0.02 inches, about 0.025 inches, about 0.03 inches, ranges between such values, etc.).

The film may comprise a plurality of pores or holes or apertures extending through the film. The film may be formed by weaving or braiding filaments or membranes and the pores may be spaces between the filaments or membranes. The filaments or membranes may comprise the same material or may include other materials (e.g., polymers, non-polymer materials such as metal, alloys such as nitinol, stainless steel, etc.). The pores of the filter element 33 are configured to allow fluid (e.g., blood) to pass through the filter element 33 and to resist the passage of embolic material that is carried by the fluid. The pores can be circular, elliptical, square, triangular, or other geometric shapes. Certain shapes such as an equilateral triangular, squares, and slots may provide geometric advantage, for example restricting a part larger than an inscribed circle but providing an area for fluid flow nearly twice as large, making the shape more efficient in filtration verses fluid volume. The pores may be laser drilled into or through the filter element 33, although other methods are also possible (e.g., piercing with microneedles, loose braiding or weaving). The pores may have a lateral dimension (e.g., diameter) between about 10 micron (μm) and about 1 mm (e.g., no more than about 10 μm, about 50 μm, about 100 μm, about 150 μm, about 200 μm, about 250 μm, about 300 μm, about 400 μm, about 500 μm, about 750 μm, about 1 mm, ranges between such values, etc.). Other pore sizes are also possible, for example depending on the desired minimum size of material to be captured.

The material of the filter element 33 may comprise a smooth and/or textured surface that is folded or contracted into the delivery state by tension or compression into a lumen. A reinforcement fabric may be added to or embedded in the filter element 33 to accommodate stresses placed on the filter element 33 during compression. A reinforcement fabric may reduce the stretching that may occur during deployment and/or retraction of the filter assembly 32. The embedded fabric may promote a folding of the filter to facilitate capture of embolic debris and enable recapture of an elastomeric membrane. The reinforcement material could comprise, for example, a polymer and/or metal weave to add localized strength. The reinforcement material could be imbedded into the filter element 33 to reduce thickness. For example, imbedded reinforcement material could comprise a polyester weave mounted to a portion of the filter element 33 near the longitudinal elements of the frame 31 where tensile forces act upon the frame 31 and filter element 33 during deployment and retraction of the filter assembly 32 from the outer sheath 42.

In some cases, the filter assembly 32 may include a self-expanding filter assembly (e.g., comprising a superelastic material with stress-induced martensite due to confinement in the outer sheath 42). The filter assembly 32 may comprise a shape-memory material configured to self-expand upon a temperature change (e.g., heating to body temperature). The filter assembly 32 may comprise a shape-memory or superelastic frame (e.g., comprising a distal end hoop comprising nitinol) and a microporous material (e.g., comprising a polymer including laser-drilled holes) coupled to the frame, for example similar to the filter assemblies described in U.S. Pat. No. 8,876,796.

The filter assembly 32 may be coupled (e.g., crimped, welded, soldered, etc.) to a distal end of a deployment wire or filter wire 52*b* via a strut or wire 52*a*. When both or all of the filter wire 52*a* and the strut 52*a* are provided, the filter wire 52*b* and the strut 52*a* may be coupled within the outer sheath 42 proximal to the filter assembly 30 using a crimp mechanism. In other embodiments, the filter wire 52*b* and the strut 52*a* may be a single unitary structure. The filter wire 52*b* and/or strut 52*a* can comprise a rectangular ribbon, a round (e.g., circular, elliptical) filament, a portion of a hypotube, a braided structure (e.g., as described herein), combinations thereof, and the like. The filter wire 52*b* can be coupled to the handle 38 and/or the slider 40 to provide differential longitudinal movement versus the outer sheath 42, as shown by the arrows 54, which can sheathe and unsheathe the filter assembly 32 from the outer sheath 42.

The filter assembly 32 in an expanded, unconstrained state has a maximum diameter or effective diameter (e.g., if the mouth is in the shape of an ellipse) d. The diameter d can be between about 1 mm and about 15 mm (e.g., at least about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, ranges between such values, etc.). In some embodiments (e.g., when the filter assembly is configured to be positioned in the left subclavian artery), the diameter d is between about 7 mm and about 12 mm (e.g., about 7 mm, about 8 mm, about 9 mm, about 10 mm, about 11 mm, about 12 mm, ranges between such values, etc.). In some embodiments (e.g., when the filter assembly is configured to be positioned in the left vertebral artery), the diameter d is between about 2 mm and about 4.5 mm (e.g., about 2 mm, about 2.5 mm, about 3 mm, about 3.5 mm, about 4 mm, about 4.5 mm, ranges between such values, etc.). Other diameters d or other types of lateral dimensions are also possible. Different diameters d can allow treatment of a selection of subjects having different vessel sizes.

The filter assembly 32 has a maximum length 1. The length 1 can be between about 7 mm and about 50 mm (e.g., at least about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 30 mm, about 35 mm, about 40 mm, about 45 mm, about 50 mm, ranges between such values, etc.). Other lengths 1 are also possible, for example based on the diameter or effective diameter d. For example, the length 1 of the filter assembly 32 may increase as the diameter d increases, and the length 1 of the filter assembly 32 may decrease as the diameter d decreases. A distance from an apex of the mouth of the filter assembly 32 to an elbow in the frame may be about 35 mm. Different lengths 1 can allow treatment of a selection of subjects having different vessel sizes.

The inner member 50 may be optional, but can provide additional uses and/or advantages in combination with the filter assembly 32. For example, the inner member 50 may comprise a guidewire lumen (not explicitly shown), allowing the device 30 to be tracked over a guidewire 56 without contacting the filter assembly 32. For another example, a lumen of the inner member 50 may be fluidly coupled to the flush port 44, which can allow flushing of fluid through the inner member 50, for example to remove air. For yet another example, a lumen of the inner member 50 may be connected to an arterial pressure monitoring device, allowing measurement of pressure proximate to the location of the filter assembly 32.

The distal portion 36 may include fluoroscopic markers one or more 58*a*, 58*b* to aid a user in positioning the device 30, deploying the filter assembly 32, utilizing the inner member 50, etc. A fluoroscopic marker 58*b* may be positioned is proximate to a distal end of the outer sheath 42. Another fluoroscopic marker (not explicitly shown) may be positioned proximate to a proximal end of the filter assembly 32. In some cases, another fluoroscopic marker 58*b* maybe proximate to a distal end of the filter assembly 32. Another fluoroscopic marker (not explicitly shown) may be proximate to a distal end of the inner member 50. The fluoroscopic markers may comprise a radiopaque material (e.g., iridium, platinum, tantalum, gold, palladium, tungsten, tin, silver, titanium, nickel, zirconium, rhenium, bismuth, molybdenum, combinations thereof, and the like). More or fewer fluoroscopic markers are also possible.

The protection device 30 is illustrated as comprising a guidewire 56 therethrough, although the guidewire 56 may be characterized as being separate from the protection device 30, for example independently sold, packaged, and/or directed. The guidewire 56 may extend through a lumen of the outer sheath 42 or the inner member 50. The lumen of the outer sheath 42 or the inner member 50 (if so provided) may be configured to receive a guidewire 56 having a diameter between about 0.014 inches (0.356 mm) and about 0.025 inches (0.635 mm). The guidewire 56 may extend through a lumen of the filter assembly 32. For example, the protection device 30 may be tracked over the guidewire 56 to position the protection device 30 at a desired location.

The filter assembly 32 may be positioned, for example, in the left subclavian artery 16, to protect the cerebral vasculature (e.g., the left vertebral artery 24) from embolic debris during an endovascular procedure such as TAVI. While the procedure described positioning the first filter assembly 32 in the left subclavian artery, the method is not limited to positioning the first filter assembly 32 within the left subclavian artery, the first filter assembly 32 may be positioned within other arteries (or other lumens), as desired. The filter assembly 32 may be positioned in the left subclavian artery 16 upstream of the left vertebral artery 24. The user may choose a protection device 30 comprising a proximal-facing filter assembly 32 having a diameter appropriate for the artery (or other lumen) in which it is to be deployed, for example, but not limited to, between about 7 mm and about 12 mm for the left subclavian artery 16. The protection device 30 may be packaged in a sterile coiled packaging. The protection device 30 may comprise an outer sheath 42 having a diameter of about 5 Fr (approximately 1.67 mm). The outer sheath 42 may include a curvature, for example complementing the size and orientation of the filter assembly 32. The outer sheath 42 may be steerable (e.g., a pull wire-controlled sheath).

Lumens of the protection device 30, for example a lumen of the outer sheath 42 and a lumen of the inner member 50, may be flushed (e.g., using saline) once or several times before, during, and/or after the procedure. The filter assembly 32 of the protection device 30 may be flushed and/or submerged (e.g., in a bowl of saline). Flushing and/or submerging of the filter assembly 32 may be with the filter assembly 32 in the outer sheath 42 (e.g., in the compressed state) and/or with the filter assembly 32 out of the outer sheath 42 (e.g., in the deployed state). If the filter assembly 32 is flushed and/or submerged in the deployed state, the filter assembly 32 may be compressed into the outer sheath 42 before use.

An artery in the right arm is accessed, for example using a 5 Fr introducer. The guidewire 56 (e.g., having a diameter between about 0.014 inches and about 0.25 inches) is steered, into or towards the right subclavian artery 22, then into the innominate artery 12, then into the aortic arch 10, and finally into the left subclavian artery 16. In some cases, a distal end of the guidewire 56 may be curved (e.g., a pigtail curve) to facilitate navigation from the right subclavian artery 22 to the left subclavian artery 16. A proximal end of the guidewire may be inserted into a distal end of the protection device 30, for example into a distal end of an inner member 50. During navigation through the vasculature, the filter assembly 32 may be disposed within a lumen of the outer sheath and held in a collapsed position therein until the filter assembly 32 advanced distally from the outer sheath 42 and/or the outer sheath 42 is proximally retracted relative to the filter assembly 32. The protection device 30 may be tracked over the guidewire until the distal end of the protection device 30 extends beyond a distal end of the introducer. In some implementations, the guidewire and the protection device 30 may be tracked together, with the guidewire leading the device 30 (e.g., advance the guidewire a distance, then advance the device 30 over the guidewire approximately the same distance). In some cases, where the guidewire and the inner member 50 may both be floppy or lack rigidity, they may be introduced inside the outer sheath 42 and then advanced ahead of the device 30 in the vasculature. The guidewire may be advanced at least about 6 centimeters (cm) distal to the distal end of the protection device 30.

The protection device 30 may be tracked or distally advanced over the guidewire until the proximal end of the protection device 30 (e.g., the opening 35) is at a desired location such as proximate to the left subclavian artery ostium 17, just above the aortic arch 10. Tracking of the protection device 30 may be performed under fluoroscopy, for example using radiopaque markers (e.g., at a distal end of the outer sheath 42 and/or the inner member 50) and/or radiopaque fluid or contrast media. Radiopaque fluid may be provided through the inner member 50 and/or the outer sheath 42. The protection device 30 may be positioned so that the filter assembly 32 is upstream of the left vertebral artery 24 or proximate to the ostium 17 so that the filter assembly 32 can inhibit or prevent embolic material from entering the cerebral vasculature through the left vertebral artery 24. Using terminology of the procedure rather than blood flow, the protection device 30 is preferably positioned so that the filter assembly 32 is proximal to the point in the left subclavian artery 16 where the left vertebral artery 24 branches off. However, it is contemplated that positioning may be based on available anatomy.

Once the protection device 30 is in position, the filter assembly 32 may be deployed from the outer sheath 42. For example, the outer sheath 42 may be proximally retracted and/or the filter assembly 32 may be distally advanced. Radiopaque markers, for example on the filter assembly 32 can help determine when the filter assembly 32 achieves a deployed state. Differential longitudinal movement of the filter assembly 32 and the outer sheath 42 can cease upon full or appropriate deployment of the filter assembly 32. Apposition of the filter assembly 32 with sidewalls of the left subclavian artery 16 can be verified, for example using radiopaque fluid or contrast media. Radiopaque fluid may be provided through the inner member 50. If the radiopaque fluid is able to flow between the frame of the filter assembly 32 and the sidewalls of the left subclavian artery 16, then the filter assembly 32 may be improperly positioned (e.g., indicative of inadequate deployment, inadequate sizing, calcium, etc.). The filter assembly 32 may be retracted back into the outer sheath 42 and redeployed, or a different protection device may be used.

After positioning of the protection device 30, the outer sheath 42 and the inner member 50 may be withdrawn while the filter wire 52b and/or strut 52a are left in place. It is contemplated that the filter wire 52b and/or strut 52a may function as a guidewire to direct the outer sheath 42 back to the filter assembly 32 when removal of the filter assembly 32 is desired. Alternatively, or additionally, the guidewire 56 may be left in place during the endovascular procedure (e.g., TAVI, TAVR, TAMI, TAMR, SAVR, other surgical valve repair, implantation, or replacement, cardiac ablation, cardiac bypass surgery, etc.). In some embodiments, the inner member 50 may be retracted to a position suitable for monitoring or sensing blood pressure. For example, a blood pressure monitoring device can be connected in fluid communication to the inner member 50 (e.g., using a luer fitting). In embodiments in which the protection device lacks an inner member, blood pressure may be monitored or sensed by connecting a blood pressure monitoring device to the outer sheath 42.

The protection devices described herein may be used alone or in combination with other protection devices. For example, a second protection device as described herein may be advanced via the right subclavian artery and positioned in both the innominate artery 12 and the left common carotid artery 14, providing protection to the right carotid artery, the right vertebral artery, and the left carotid artery 14. For another example, an aortic arch filter or deflector such as the Embrella Embolic Deflector System, the TriGuard embolic protection system, or the like may be placed across the great branch artery ostia and/or apposing sidewalls of the aortic arch upstream of at least one of the great branch artery ostia. For another example, the filter systems and methods described in U.S. Pat. No. 8,876,796 can be used in combination with the protection devices described herein to further protect the cerebral vasculature during an endovascular procedure.

Figure 1B:
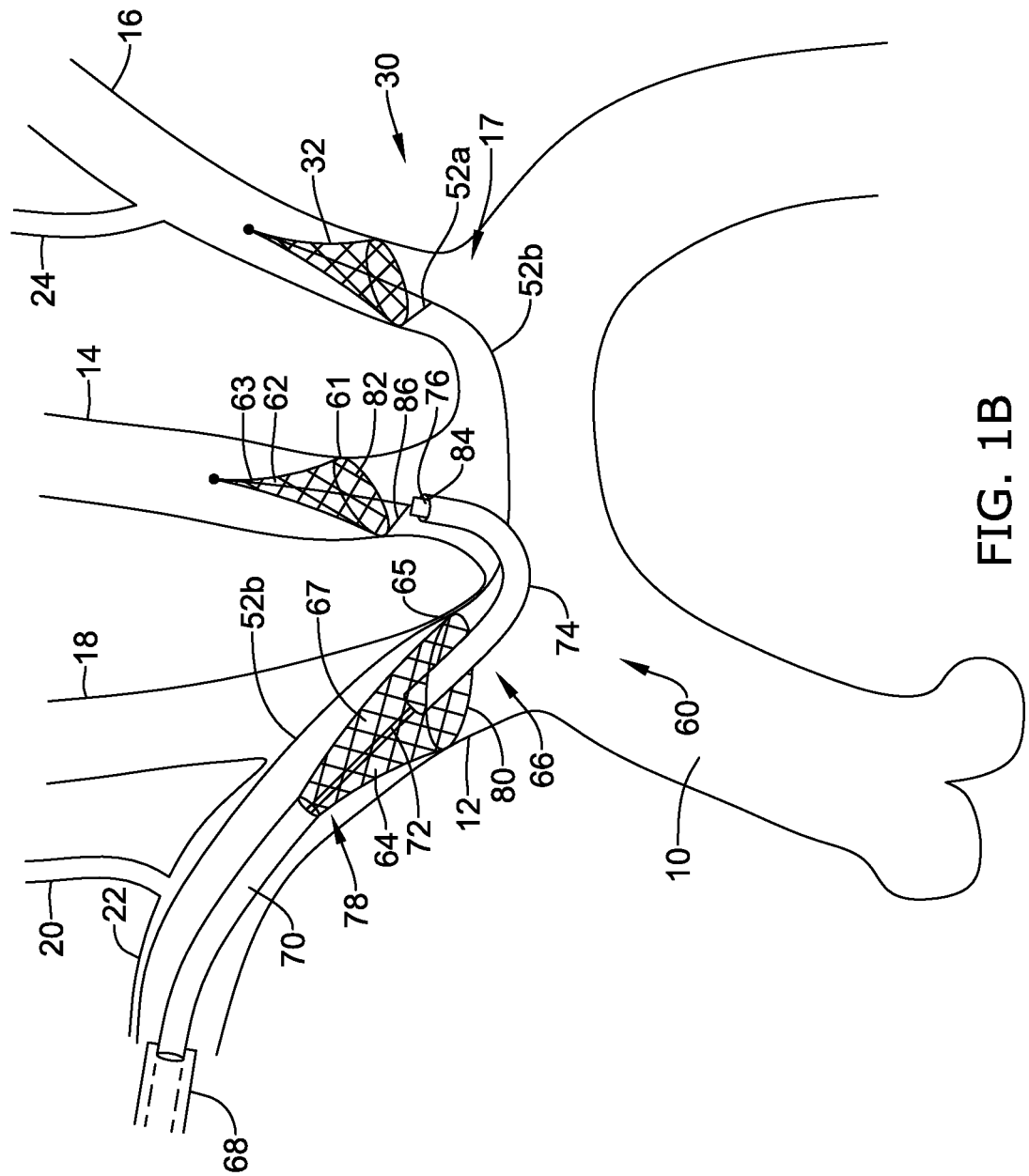

For example, after the first filter assembly 32 has been positioned, a second protection device, or filter system, 60 may be deployed in the innominate artery 12 and the left common carotid artery 14, as shown in FIG. 1B. FIG. 1B illustrates an example distal portion of a second protection device 60 having two filter assemblies 62, 64 in a deployed state. Illustrative protection devices including two filter assemblies are described in commonly assigned U.S. Pat. No. 9,492,264, the entirety of which is hereby incorporated by reference.

The second protection device 60 may include a distal end region 66 including at least the filter assembles 62, 64 and a proximal end region (not explicitly shown) coupled to a handle (not explicitly shown) configured to remain outside the body. In some cases, the handle of the second protection device 60 may be similar in form and function to the handle 38 described herein. The distal end region 66 may include a proximal sheath 68, a proximal shaft 70 coupled to an expandable proximal filter assembly 64, a distal shaft 72 coupled to a distal articulatable sheath 74, a distal filter 62, and guiding member 76.

The proximal shaft 70 is co-axial with proximal sheath 68, and a proximal region 78 of proximal filter assembly 64 is secured to proximal shaft 70. In its collapsed configuration (not explicitly shown), the proximal filter assembly 64 may be disposed within proximal sheath 68 and is disposed distally relative to proximal shaft 70. The proximal sheath 68 may be axially (distally and proximally) movable relative to proximal shaft 70 and the proximal filter assembly 64. The system 60 may also include a distal sheath 74 secured to a distal region of distal shaft. The distal shaft 72 may be co-axial with the proximal shaft 70 and the proximal sheath 68. The distal sheath 74 and distal shaft 72 may be secured to one another axially movable relative to proximal sheath 68, the proximal shaft 70 and the proximal filter assembly 64. The system 60 may also include a distal filter assembly 62 carried by the guiding member 76. While not explicitly shown, the distal filter assembly 62 may be maintained in a collapsed configuration within the distal sheath 74. The guiding member 76 may be coaxial with distal sheath 74 and distal shaft 72 as well as proximal sheath 68 and proximal shaft 70. The guiding member 76 may be axially movable relative to distal sheath 74 and distal shaft 72 as well as proximal sheath 68 and proximal shaft 70. The proximal sheath 68, the distal sheath 74, and the guiding member 76 may each be adapted to be independently moved axially relative to one other. That is, the proximal sheath 68, the distal sheath 74, and the guiding member 76 are adapted for independent axial translation relative to each of the other two components. It is contemplated that the handle may include control elements (such as, but not limited to, slides, switches, buttons, dials, etc.) configured to individually actuate the proximal sheath 68, the distal sheath 74, and the guiding member 76.

The proximal filter assembly 64 may include a support element or frame 65 and filter element 67. Similarly, the distal filter assembly 62 includes support element 61 and filter element 63. The frames 61, 65 may be similar in form and function to the frame 31 described herein. Similarly, the filter elements 63, 67 may be similar in form and function to the filter element 33 described herein. The support elements 61, 65 generally provide expansion support to the filter elements 63, 67 in their respective expanded configurations, while the filter elements 63, 67 are adapted to filter fluid, such as blood, and trap particles flowing therethrough. The expansion supports 61, 65 are adapted to engage the wall of the lumen in which they are expanded. The filter elements 63, 67 have pores therein that are sized to allow the blood to flow therethrough, but are small enough to prevent unwanted foreign particles from passing therethrough. The foreign particles are therefore trapped by and within the filter elements 63, 67.

As shown in FIG. 1B, the proximal filter 64 has a generally distally-facing opening 80, and the distal filter 62 has a generally proximally-facing opening 82 relative to the device 60. The filter assemblies 62, 64 can be thought of as facing opposite directions. As described in more detail below, the distal sheath 74 may be adapted to be steered, or bent, relative to the proximal sheath 68 and the proximal filter 64. As the distal sheath 74 is steered, the relative directions in which the openings face will be adjusted. Regardless of the degree to which the distal sheath 74 is steered, the filter assemblies 62, 64 are still considered to having openings facing opposite directions. For example, the distal sheath 74 could be steered to have an approximately 720 degree bend, in which case the filter assemblies 62, 64 would have openings 82, 80 facing in substantially the same direction, as shown in FIG. 1B. The directions of the filter openings 80, 82 are therefore described if the system were to assume a substantially straightened configuration (not explicitly shown). The proximal filter element 67 may taper down in the proximal direction from support element 65, while the distal filter element 63 may taper down in the distal direction from support element 61. A fluid, such as blood, flows through the opening and passes through the pores in the filter elements 63, 67, while the filter elements 63, 67 are adapted to trap foreign particles therein and prevent their passage to a location downstream of the filter assemblies.

The filters 62, 64 may be secured to separate system components. For example, the proximal filter assembly 64 is secured to the proximal shaft 70, while the distal filter assembly 62 is secured to guiding member 76. In FIG. 1B, the filters 62, 64 are secured to independently actuatable components. This may allow the filters 62, 64 to be independently positioned and controlled. Additionally, the filters 62, 64 may be collapsed within two different tubular members in their collapsed configurations. For example, the proximal filter assembly 64 is collapsed within proximal sheath 68, while the distal filter assembly 62 is collapsed within distal sheath 74. In the system's delivery configuration, the filter assemblies 62, 64 are axially-spaced from one another. For example, in FIG. 1B, the distal filter assembly 62 is distally-spaced relative to proximal filter assembly 64. However, in an alternative embodiment, the filter assemblies 62, 64 may be positioned such that a first filter is located within a second filter.

In some embodiments, the distal sheath 74 and the proximal sheath 68 have substantially the same outer diameter. When the filter assemblies 62, 64 are collapsed within the sheaths, the sheath portion of the system 60 therefore has a substantially constant outer diameter, which can ease the delivery of the system 60 through the patient's body and increase the safety of the delivery. The distal and proximal sheaths 74 and 68 may have substantially the same outer diameter, both of which have larger outer diameters than the proximal shaft 70. The proximal shaft 70 may have a larger outer diameter than the distal shaft 72, wherein the distal shaft 72 is disposed within the proximal shaft 70. The guiding member 76 may have a smaller diameter than the distal shaft 72. In some embodiments the proximal and distal sheaths 68, 74 have an outer diameter between 3 French (F) and 70 F. In certain embodiments, the outer diameter is between 4 F and 8 F. In still other embodiments, the outer diameter is between 4 F and 6 F. In some embodiments, the sheaths 68, 74 have different outer diameters. For example, the proximal sheath 68 can have a size of 6 F, while the distal sheath 74 has a size of 5 F. In an alternate embodiment the proximal sheath 68 is 5 F and the distal sheath 74 is 4 F. These are just examples and are not intended to limit the sheaths 68, 74 to a particular size. A distal sheath 74 with a smaller outer diameter than the proximal sheath 68 reduces the delivery profile of the system 60 and can ease delivery. In some methods of use, the filter system 60 is advanced into the subject through an incision made in the subject's right radial artery, or alternatively the right brachial artery. In a variety of medical procedures a medical instrument is advanced through a subject's femoral artery, which is larger than the right radial artery. A delivery catheter used in femoral artery access procedures has a larger outer diameter than would be allowed in a filter system advanced through a radial artery. Additionally, in some uses the filter system is advanced from the right radial artery into the aorta via the brachiocephalic trunk. The radial artery has the smallest diameter of the vessels through which the system is advanced. The radial artery therefore limits the size of the system that can be advanced into the subject when the radial artery is the access point. The outer diameters of the systems described herein, when advanced into the subject via a radial artery, are therefore smaller than the outer diameters of the guiding catheters (or sheaths) typically used when access is gained via a femoral artery.

The system 60 may be delivered to the left carotid artery 14 and the innominate artery 12 in a delivery configuration. The system's delivery configuration generally refers to the configuration when both filter assemblies 62, 64 are in collapsed configurations within the system. The distal articulating sheath 74 may be independently movable with 3 degrees of freedom relative to the proximal sheath 68 and proximal filter 64. In some embodiments, the proximal sheath 68 and the distal sheath 74 may be releasably coupled together. For example, the proximal sheath 68 can be coupled to the distal sheath 74 using an interference fit, a friction fit, a spline fitting, end to end butt fit or any other type of suitable coupling between the two sheaths 68, 74. When coupled together, the components move as a unit. For example, the proximal sheath 68, the proximal shaft 70, the proximal filter 64, the distal shaft 72, and the distal filter 62 will rotate and translate axially (in the proximal or distal direction) as a unit. When proximal sheath 68 is retracted to allow proximal filter 64 to expand, the distal sheath 74 can be independently rotated, steered, or translated axially (either in the proximal direction or distal direction). The distal sheath 74 therefore has 3 independent degrees of freedom: axial translation, rotation, and steering. The adaptation to have 3 independent degrees of freedom is advantageous when positioning the distal sheath 74 in a target location, details of which are described below.

The system 60 is advanced into the subject's right radial artery through an incision in the right arm, or alternately through the right brachial artery. For example, the system 60 may be advanced through the same incision as the first system 30. The system is advanced through the right subclavian artery 22 and into the brachiocephalic or innominate artery 12, and a portion of the system is positioned within aortic arch 10. The proximal sheath 68 is retracted proximally to allow proximal filter support element 65 to expand to an expanded configuration against the wall of the innominate artery 12, as is shown in FIG. 1B. The proximal filter element 67 is secured either directly or indirectly to support element 65 and is therefore reconfigured to the configuration shown in FIG. 1B. The position of distal sheath 74 can be substantially maintained while proximal sheath 68 is retracted proximally. Once expanded, the proximal filter assembly 64 filters blood traveling through the innominate artery 12, and therefore filters blood traveling into the right common carotid artery 18 and the right vertebral artery 20. The expanded proximal filter assembly 64 is therefore in position to prevent foreign particles from traveling into the right common carotid artery 18 and the right vertebral artery 20 and into the cerebral vasculature.

The distal sheath 74 is then steered, or bent, and the distal end 84 of the distal sheath 74 is advanced into the left common carotid artery 14. The guiding member 76 is thereafter advanced distally relative to distal sheath 74, allowing the distal support element 61 to expand from a collapsed configuration to a deployed configuration against the wall of the left common carotid artery 14, as shown in FIG. 1B. The distal filter element 63 is also reconfigured into the configuration shown in FIG. 1B. Once expanded, the distal filter assembly 62 filters blood traveling through the left common carotid artery 14. In some embodiments, the distal filter assembly 62 may be deployed prior to the deployment of the proximal filter assembly 64. The distal filter assembly 62 is therefore in position to trap foreign particles and prevent them from traveling into the cerebral vasculature. As can be seen in FIG. 1B, together the first protection system 30 and the second protection system 60 collectively trap foreign particles and prevent them from traveling into the four arteries 14, 18, 20, 24 that carry oxygenated blood to the brain.

The filter system(s) 30, 60 can thereafter be removed from the subject (or at any point in the procedure). In an exemplary embodiment, distal filter assembly 62 is first retrieved back within distal sheath 74 to the collapsed configuration. To do this, the guiding member 76 is retracted proximally relative to the distal sheath 74. This relative axial movement causes the distal sheath 74 to engage a strut or wire 86 and begin to move strut 86 towards guiding member 76. The support element 61, which is coupled to the strut 86, begins to collapse upon the collapse of the strut 86. The filter element 63 therefore begins to collapse as well. Continued relative axial movement between the guiding member 76 and the distal sheath 74 continues to collapse the strut 86, the support element 61, and the filter element 63 until the distal filter assembly 62 is retrieved and re-collapsed back within distal sheath 74 (not explicitly shown). Any foreign particles trapped within the distal filter element 63 are contained therein as the distal filter assembly 62 is re-sheathed. The distal sheath 74 is then steered into a configuration where the distal sheath 74 is generally parallel with the distal shaft 72. Said differently, the distal sheath 74 is steered such that it has generally linear orientation. The proximal sheath 70 is then advanced distally relative to proximal filter assembly 64. This causes proximal filter assembly 64 to collapse around distal shaft 72, trapping any particles within the collapsed proximal filter 67. The proximal sheath 68 continues to be moved distally towards the distal sheath 74 until the proximal sheath 68 is coupled with or nearly coupled with the distal sheath 74. The entire system 60 can then be removed from the subject.

Once the second filter system 60 has been removed from the body, the outer sheath 42 of the first filter system 30 can be advanced (e.g., over a guidewire 56 or the filter wire 52b) such that the filter assembly 32 may be retracted back into the outer sheath 42 (e.g., by distally advancing the outer sheath 42 and/or by proximally retracting the filter assembly 32). The action to re-sheathe the filter assembly 32 may by opposite to the action to unsheathe the filter assembly 32 (e.g., retraction of a slider and advancement of the slider, respectively) or may be a completely different action. The inner member 50 may be distally advanced before, during, or after re-sheathing of the filter assembly 32. Radiopaque markers, for example on the filter assembly 32 can help determine when the filter assembly 32 achieves a compressed state. Differential longitudinal movement of the filter assembly 32 and the outer sheath 42 can cease upon full or appropriate capture of the filter assembly 32. Radiopaque fluid may be provided through the inner member 50. Embolic material trapped in the filter assembly 32 may also be captured by the re-sheathing process. Once the protection device 30 is in a compressed state, the protection device 30 may be proximally retracted out of the right subclavian artery 22.

In any of the embodiments mentioned herein, the filter or filter assemblies 32, 62, 64 may alternatively be detached from the delivery catheter, and the delivery catheter removed leaving the filter 32, 62, 64 behind. The filter or filter assemblies 32, 62, 64 can be left in place permanently, or retrieved by snaring it with a retrieval catheter following a post procedure treatment period of time. Alternatively, the filter assemblies 32, 62, 64 may remain attached to the catheter, and the catheter may be left in place post procedure for the treatment period of time. That treatment period may be at least one day, one week, three weeks, five weeks or more, depending upon the clinical circumstances. Patients with an indwelling filter or filter assemblies may be administered any of a variety of thrombolytic or anticoagulant therapies, including tissue plasminogen activator, streptokinase, coumadin, heparin and others known in the art.

Figure 1C:
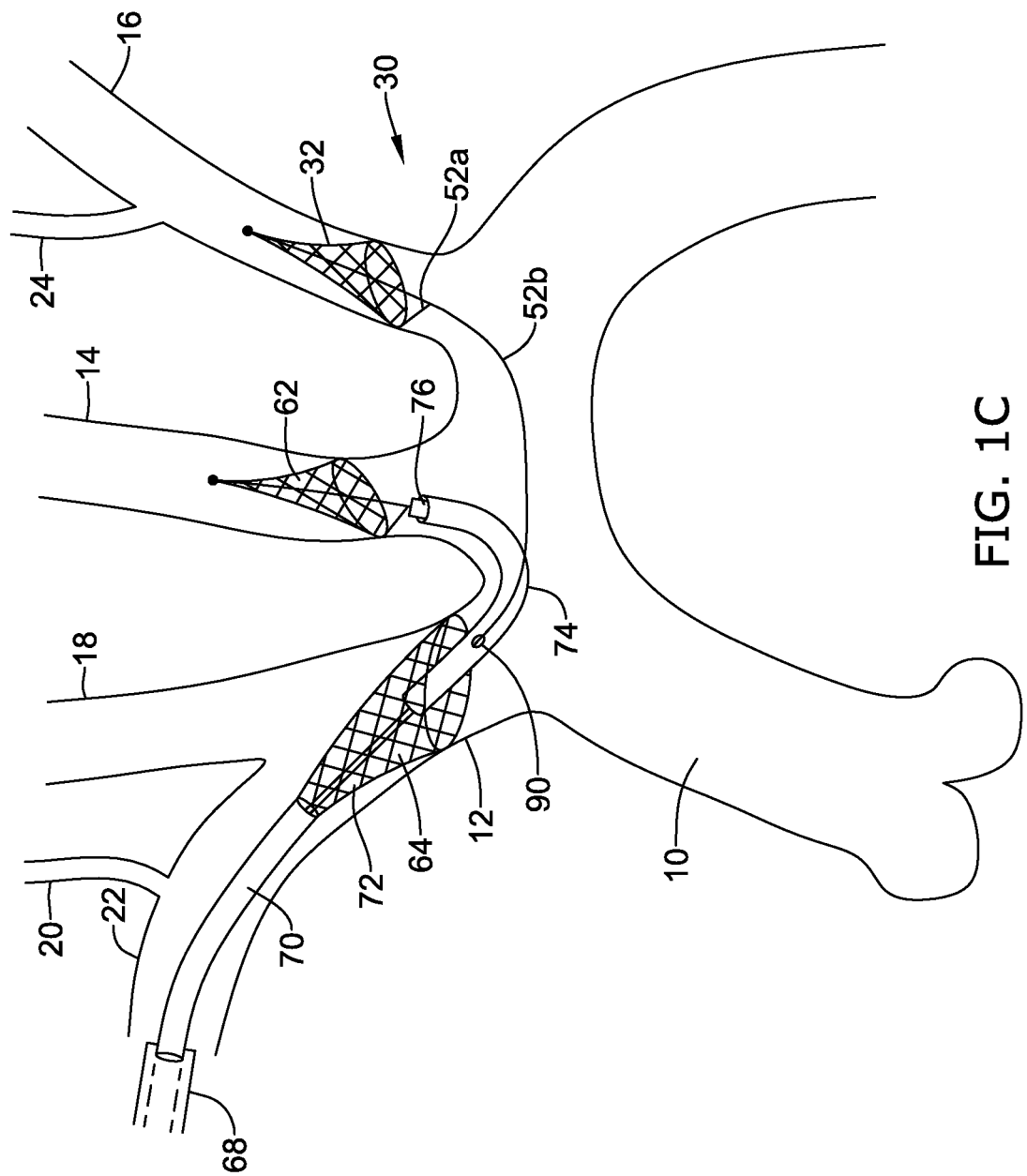
FIG. 1C illustrates an alternate embodiment of the three filter system of FIGS. 1A and 1B.

FIG. 1C illustrates an alternative embodiment for the systems of FIGS. 1A and 1B. In FIG. 1B, the filter wire 52b remains within the body (e.g., within the vasculature) but remains outside of the second filter system 60. In the embodiment of FIG. 1C, the first filter system 30 may be deployed as discussed above. The second filter system 60 may then be advanced over the filter wire 52b of the first filter system 30 via a port 90 in the distal sheath 74. The filter wire 52b is contained within a lumen of the second filter system 60 for a length less than an entirety of the length of the second first system 60 rather than running along and outside of the second filter system 60. The second filter system 60 may then be deployed as discussed above.

Figure 1D:
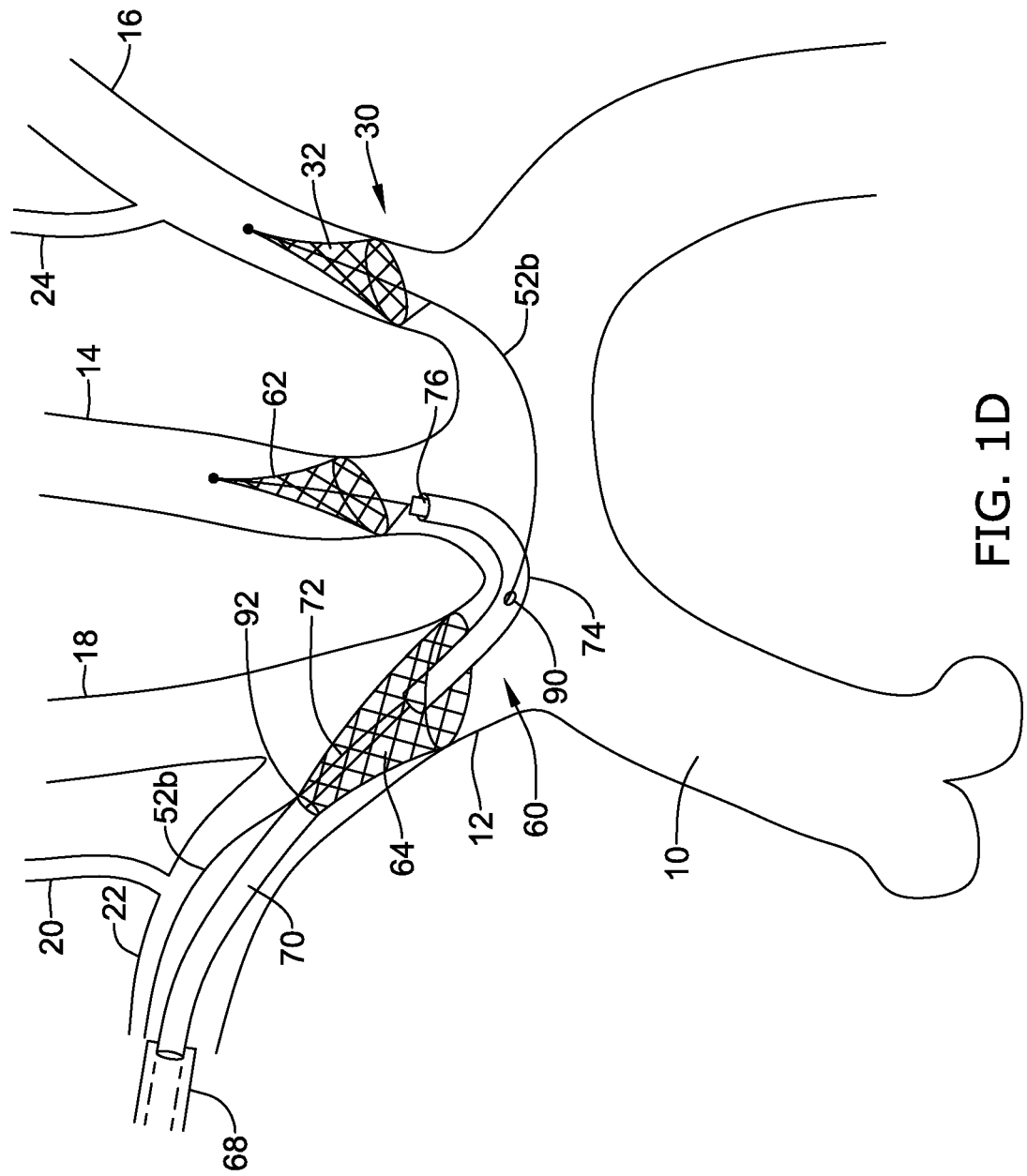
FIGS. 1D and 1E illustrate an alternate embodiment of the three filter system of FIG. 1C.
Figure 1E:
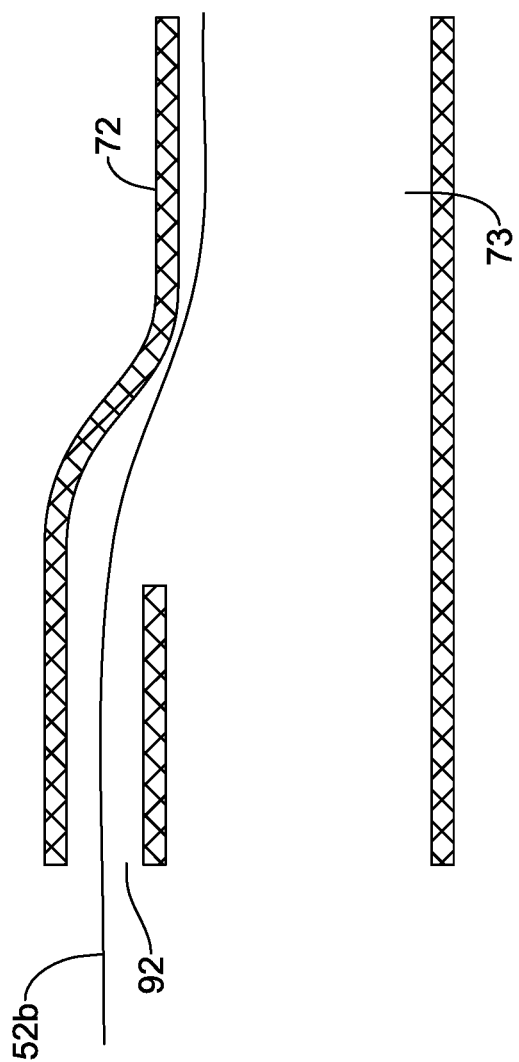

FIGS. 1D and 1E illustrate another alternative embodiment for the systems of FIGS. 1A and 1B. In the embodiment of FIG. 1D, the distal shaft 72 may include a rapid exchange port 92 which is illustrated in more detail in FIG. 1E. The rapid exchange port 92 may allow the filter wire 52b to distally exit second filter system proximal to the proximal filter assembly 64. A second port (not explicitly shown) may be formed in the second filter system 60 at a location distal to the rapid exchange port 92 to allow the filter wire 52b to enter the second filter system 60. In some cases, the filter wire 52b may enter then the second filter system through a port 90 in the distal sheath 74, although this is not required. It is contemplated that the filter wire 52b may enter through a port formed in any of the components of the second filter system 60 or through a distal opening of any of the components of the second filter system 60, as desired. It is further contemplate that the rapid exchange port 92 may be port formed in any of the components of the second filter system 60, as desired. For example, as the second filter system 60 is advanced into the vasculature, the proximal end of the filter wire 52b may inserted into the port 90 (or other suitable opening). The rapid exchange port 92 may include features that direct the proximal end of the filter wire 52b out of the rapid exchange port 92 as the second filter system 60 is distally advanced over the filter wire 52b. As can be seen in FIG. 1E, the filter wire 52b may deflected into and out of the rapid exchange port 92. It should be understood that the distal shaft 72 may include other components within the lumen 73 thereof; however, for clarity, these components are not illustrated.

Figure 2A:
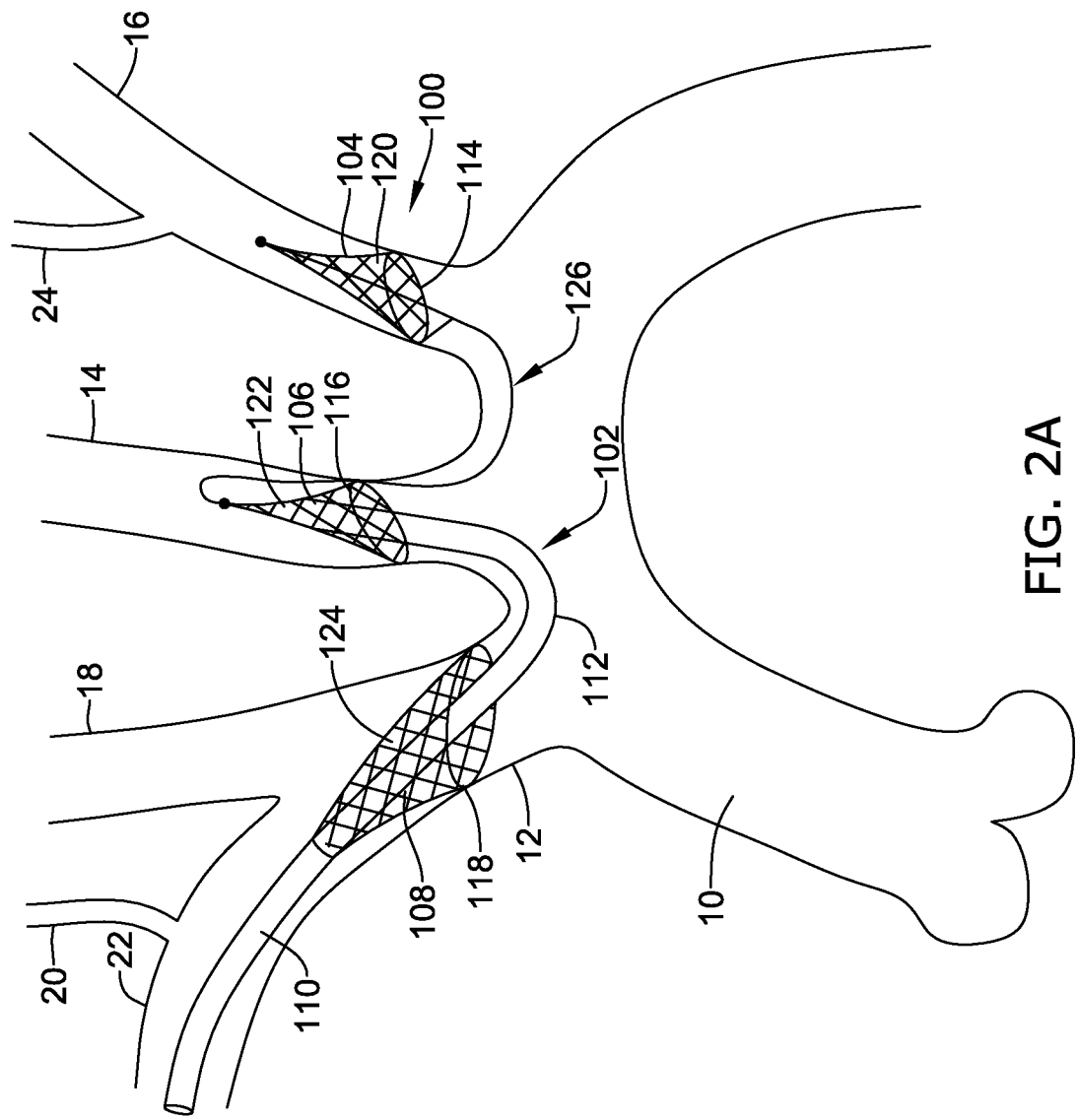
FIG. 2A illustrates another embodiment of a three filter system.

FIG. 2A illustrates another illustrative protection device, or filter system, 100 in which three filters are delivered with a single delivery device. The filter system 100 may be similar to the second filter system 60 described above. The filter system 100 may include a distal end region 102 including at least a first filter assembly 104, a second filter assembly 106, and a third filter assembly 108 and a proximal end region (not explicitly shown) coupled to a handle (not explicitly shown) configured to remain outside the body. The first filter assembly 104, second filter assembly 106, and third filter assembly 108 may each include a support member or frame 114, 116, 118 and a filter element 120, 122, 124. The support members 114, 116, 118 may be similar in form and function to the support member 31 described herein. The filter elements 120, 122, 124 may be similar in form and function to the filter element 33 described herein. In some cases, the handle of the filter system 100 may be similar in form and function to the handle 38 described herein. The distal end region 102 may include a proximal sheath 110, a proximal shaft (not explicitly shown) coupled to an expandable proximal, or third, filter assembly 108, a distal shaft 132 (see, FIG. 2B) coupled to a distal articulatable sheath 112, an intermediate, or second, filter assembly 106, a distal, or first filter assembly 104, and guiding member (not explicitly shown). As can be seen, the filter system 100 may be structurally similar to the second filter system 100 described herein and may be similarly arranged. However, in the filter system 100 illustrated in FIG. 2A, both the first filter assembly 104 and the second filter assembly 106 may be loaded into the distal sheath 112 for delivery. The first and second filter assemblies 104, 106 may be coupled together via a wire or tether 126. In some cases, the tether 126 may be made having a predetermined shape to better assist the tether 126 in seating and spanning the distance from the ostium of the left subclavian artery 16 to the left common carotid artery 14.

The system 100 is advanced into the subject's right radial artery through an incision in the right arm, or alternatively through the right brachial artery. While not explicitly shown, the system 100 may be advanced over or in conjunction with one or more guidewires. The system is advanced through the right subclavian artery 22 and into the innominate artery 12, and a portion of the system is positioned within aortic arch 10. The proximal sheath 110 is retracted proximally to allow proximal filter support element 118 to expand to an expanded configuration against the wall of the innominate artery 12, as is shown in FIG. 2A. The proximal filter element 124 is secured either directly or indirectly to support element 118 and is therefore reconfigured to the configuration shown in FIG. 2A. The position of distal sheath 112 can be substantially maintained while proximal sheath is retracted proximally. Once expanded, the proximal filter assembly 108 filters blood traveling through the innominate artery 12, and therefore filters blood traveling into the right common carotid artery 18 and the right vertebral artery 20. The expanded proximal filter assembly 108 is therefore in position to prevent foreign particles from traveling into the right common carotid artery 18 and the right vertebral artery 20 and into the cerebral vasculature.

The distal sheath 112 is then steered, or bent, and the distal end of the distal sheath 112 is advanced into the left subclavian artery 16. The guiding member (not explicitly shown) is thereafter advanced distally relative to distal sheath 112, allowing the distal support element 114 to expand from a collapsed configuration to a deployed configuration against the wall of the left subclavian artery 16, as shown in FIG. 2A. Alternatively, or additionally, the distal sheath 112 may be proximally retracted to deploy the distal filter assembly 104. The distal filter element 120 is also reconfigured into the configuration shown in FIG. 2A. Once expanded, the distal filter assembly 104 filters blood traveling through the left subclavian artery 16. The expanded distal filter assembly 104 is therefore in positioned to prevent foreign particles from traveling into the left subclavian artery 16 and the left vertebral artery 24 and into the cerebral vasculature Once the distal filter assembly 104 has been positioned in the left subclavian artery, the tether 126 may be distally advanced to provide additional length or "slack" to allow the distal sheath 112 to be repositioned. The distal sheath 112 may be manipulated to then cannulate the left common carotid artery 14. The guiding member (not explicitly shown) is thereafter advanced distally relative to distal sheath 112, allowing the intermediate support element 116 to expand from a collapsed configuration to a deployed configuration against the wall of the left common carotid artery 14, as shown in FIG. 2A. The intermediate filter element 122 is also reconfigured into the configuration shown in FIG. 2A. Once expanded, the intermediate filter assembly 106 filters blood traveling through the left common carotid artery 14. In some embodiments, the distal filter assembly 104 and the intermediate filter assembly 106 may be deployed prior to the deployment of the proximal filter assembly 108. The intermediate filter assembly 106 is therefore in position to trap foreign particles and prevent them from traveling into the cerebral vasculature. As can be seen in FIG. 2A, the protection system 100 traps foreign particles and prevent them from traveling into the four arteries 14, 18, 20, 24 that carry oxygenated blood to the brain. It is contemplated that when the procedure is completed, the insertion steps may be performed in reverse to remove the system 100.

Figure 2B:
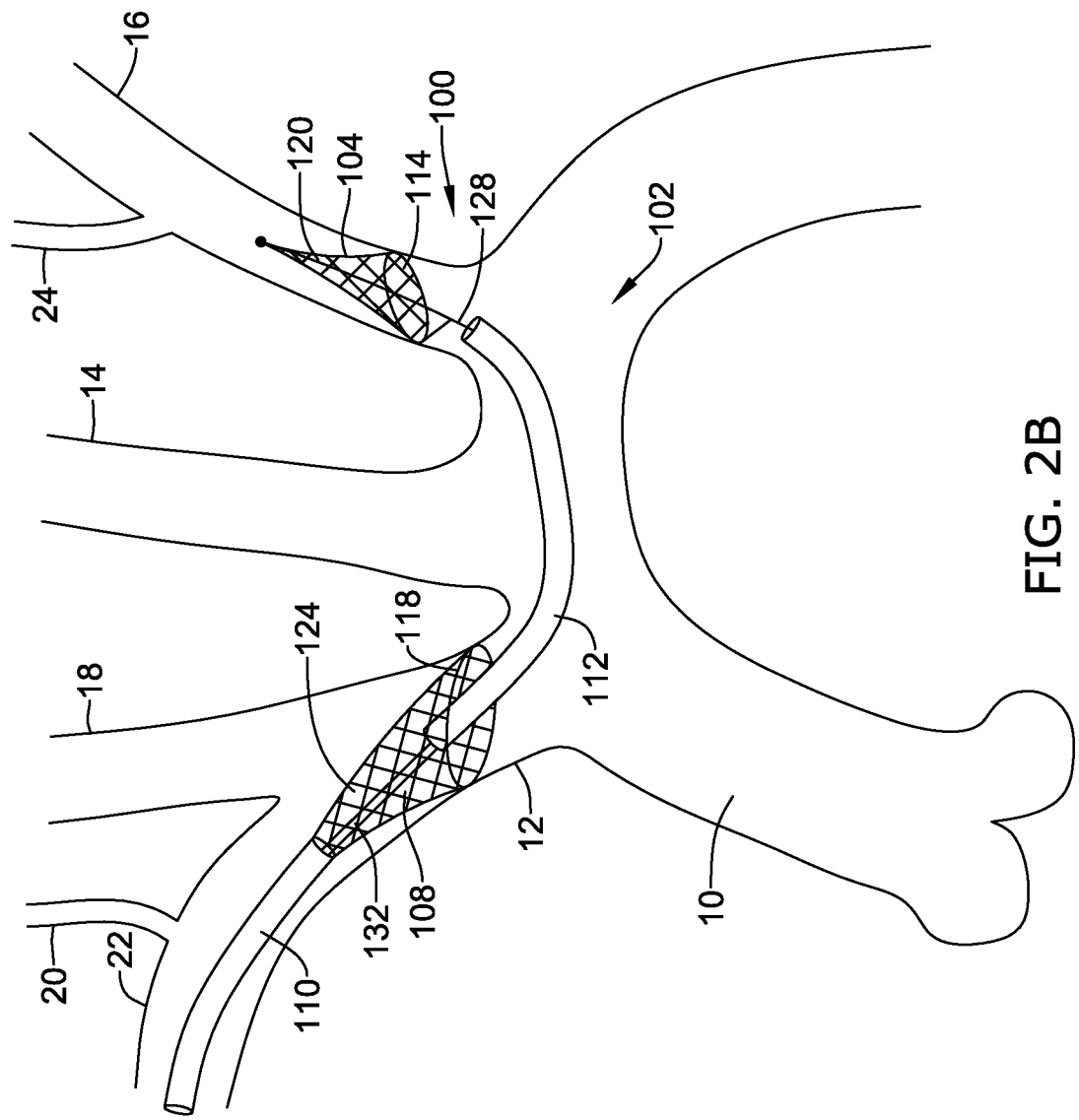
FIGS. 2B and 2C illustrate another alternate embodiment of the three filter system of FIG. 2A.
Figure 2C:
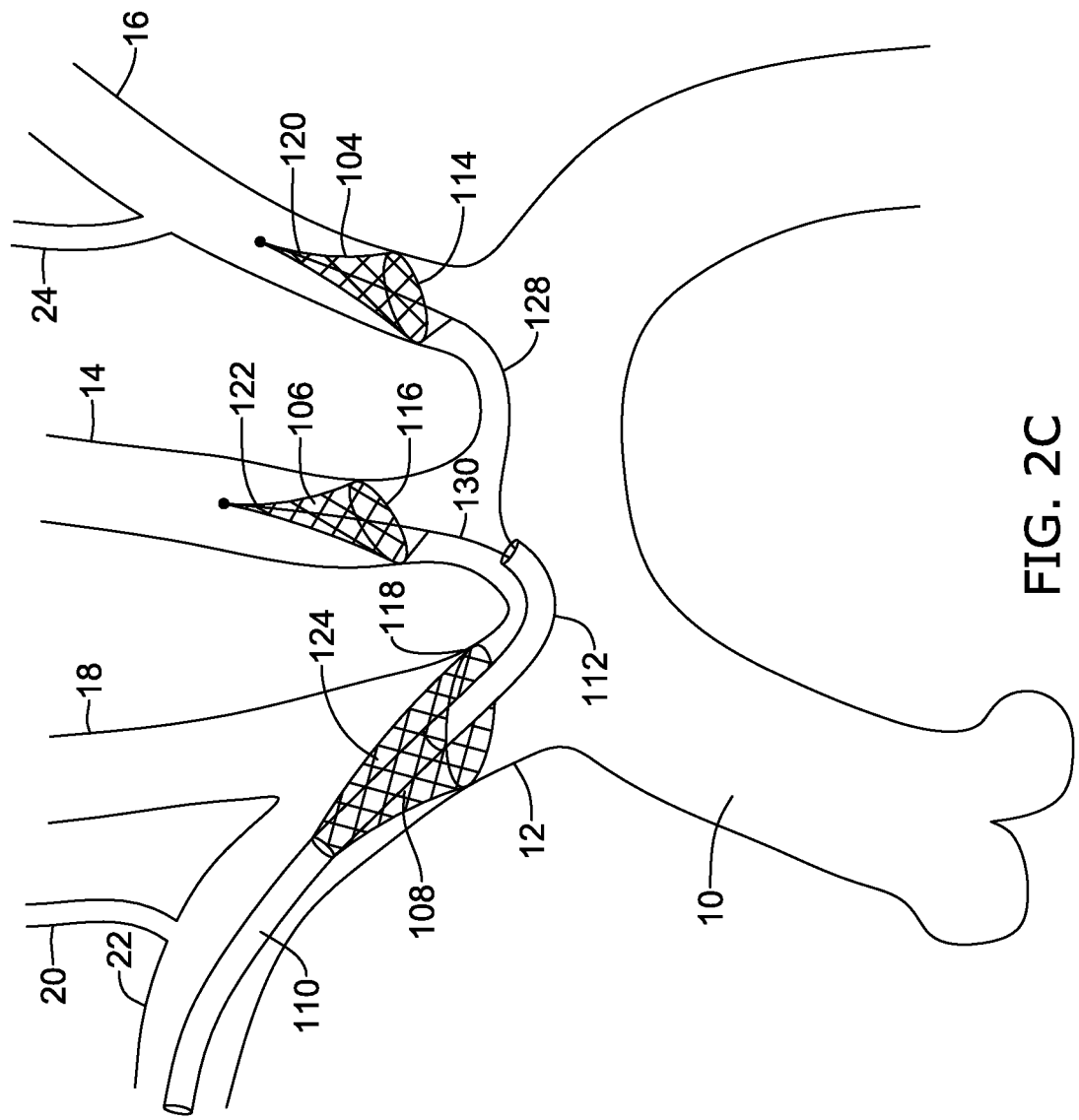

FIGS. 2B and 2C illustrate an alternative embodiment of the illustrative protection device, or filter system, 100 of FIG. 2A in which three filters are delivered with a single delivery device. In the embodiment of FIGS. 2B and 2C, the first and second filter assemblies 104, 106 each include their own filter wire 128, 130. For example, the first and second filter assemblies 104, 106 may be free from the tether 126 illustrated in FIG. 2A. The embodiment of FIGS. 2B and 2C may be deployed in a similar manner to the embodiment of FIG. 2A.

The system 100 is advanced into the subject's right radial artery through an incision in the right arm. The system is advanced through the right subclavian artery 22 and into the innominate artery 12, and a portion of the system is positioned within aortic arch 10. The proximal sheath 110 is retracted proximally to allow proximal filter support element 118 to expand to an expanded configuration against the wall of the innominate artery 12, as is shown in FIG. 2B. The proximal filter element 124 is secured either directly or indirectly to support element 118 and is therefore reconfigured to the configuration shown in FIG. 2B. The position of distal sheath 112 can be substantially maintained while proximal sheath is retracted proximally. Once expanded, the proximal filter assembly 108 filters blood traveling through the innominate artery 12, and therefore filters blood traveling into the right common carotid artery 18 and the right vertebral artery 20. The expanded proximal filter assembly 108 is therefore in position to prevent foreign particles from traveling into the right common carotid artery 18 and the right vertebral artery 20 and into the cerebral vasculature.

The distal sheath 112 is then steered, or bent, and the distal end of the distal sheath 112 is advanced into the left subclavian artery 16. The guiding member (not explicitly shown) is thereafter advanced distally relative to distal sheath 112, allowing the distal support element 114 to expand from a collapsed configuration to a deployed configuration against the wall of the left subclavian artery 16, as shown in FIG. 2B. Alternatively, or additionally, the distal sheath 112 may be proximally retracted to deploy the distal filter assembly 104. The distal filter element 120 is also reconfigured into the configuration shown in FIG. 2A. Once expanded, the distal filter assembly 104 filters blood traveling through the left subclavian artery 16. The expanded distal filter assembly 104 is therefore in positioned to prevent foreign particles from traveling into the left subclavian artery 16 and the left vertebral artery 24 and into the cerebral vasculature Once the distal filter assembly 104 has been positioned in the left subclavian artery, the distal sheath 112 may be manipulated to then cannulate the left common carotid artery 14. The guiding member (not explicitly shown) is thereafter advanced distally relative to distal sheath 112, allowing the intermediate support element 116 to expand from a collapsed configuration to a deployed configuration against the wall of the left common carotid artery 14, as shown in FIG. 2C. The intermediate filter element 122 is also reconfigured into the configuration shown in FIG. 2C. Once expanded, the intermediate filter assembly 106 filters blood traveling through the left common carotid artery 14. In some embodiments, the distal filter assembly 104 and the intermediate filter assembly 106 may be deployed prior to the deployment of the proximal filter assembly 108. The intermediate filter assembly 106 is therefore in position to trap foreign particles and prevent them from traveling into the cerebral vasculature. As can be seen in FIG. 2C, the protection system 100 traps foreign particles and prevent them from traveling into the four arteries 14, 18, 20, 24 that carry oxygenated blood to the brain.

Figure 3A:
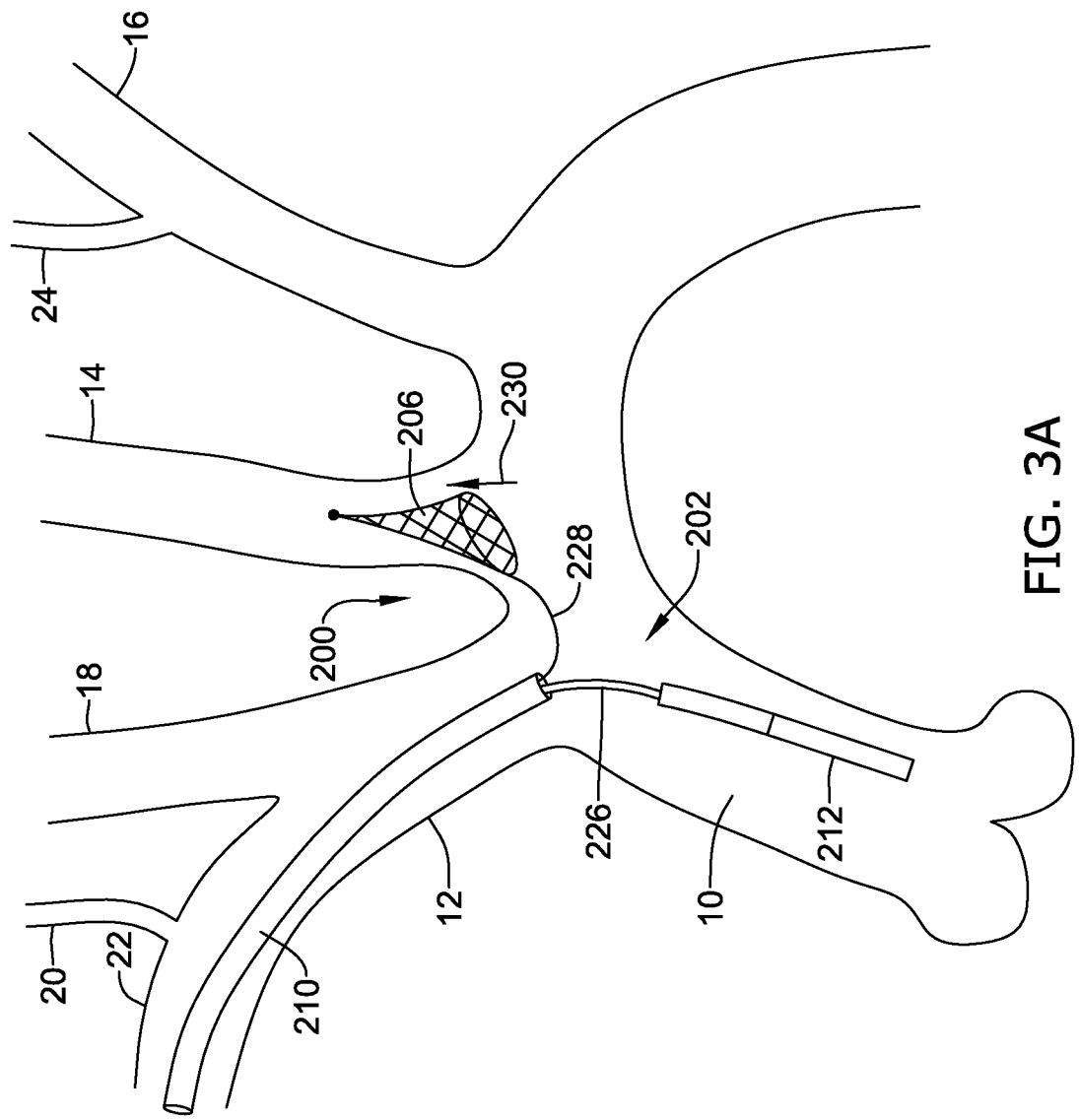
FIGS. 3A-3C illustrate another alternate embodiment of a three filter system.
Figure 3B:
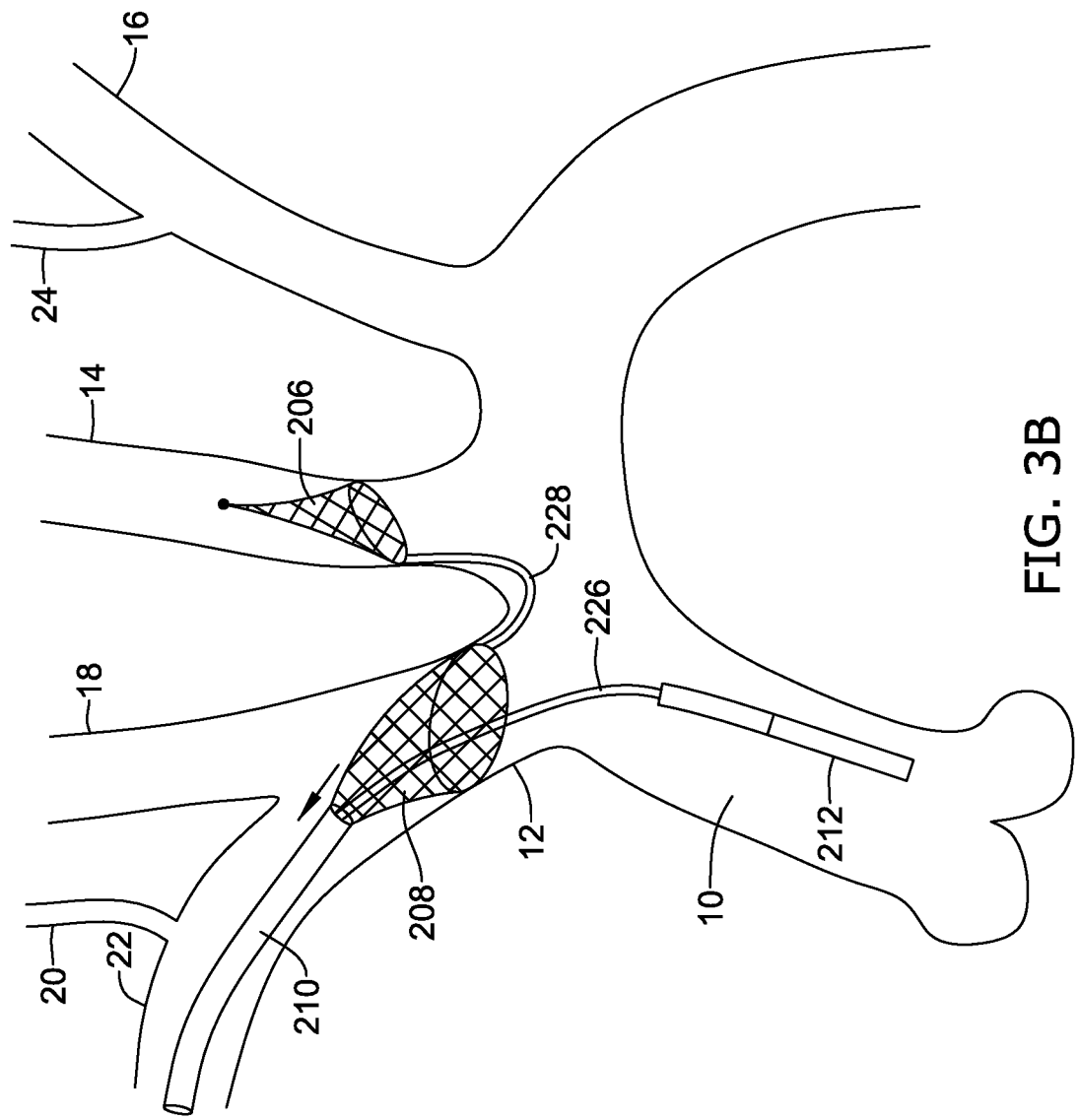
Figure 3C:
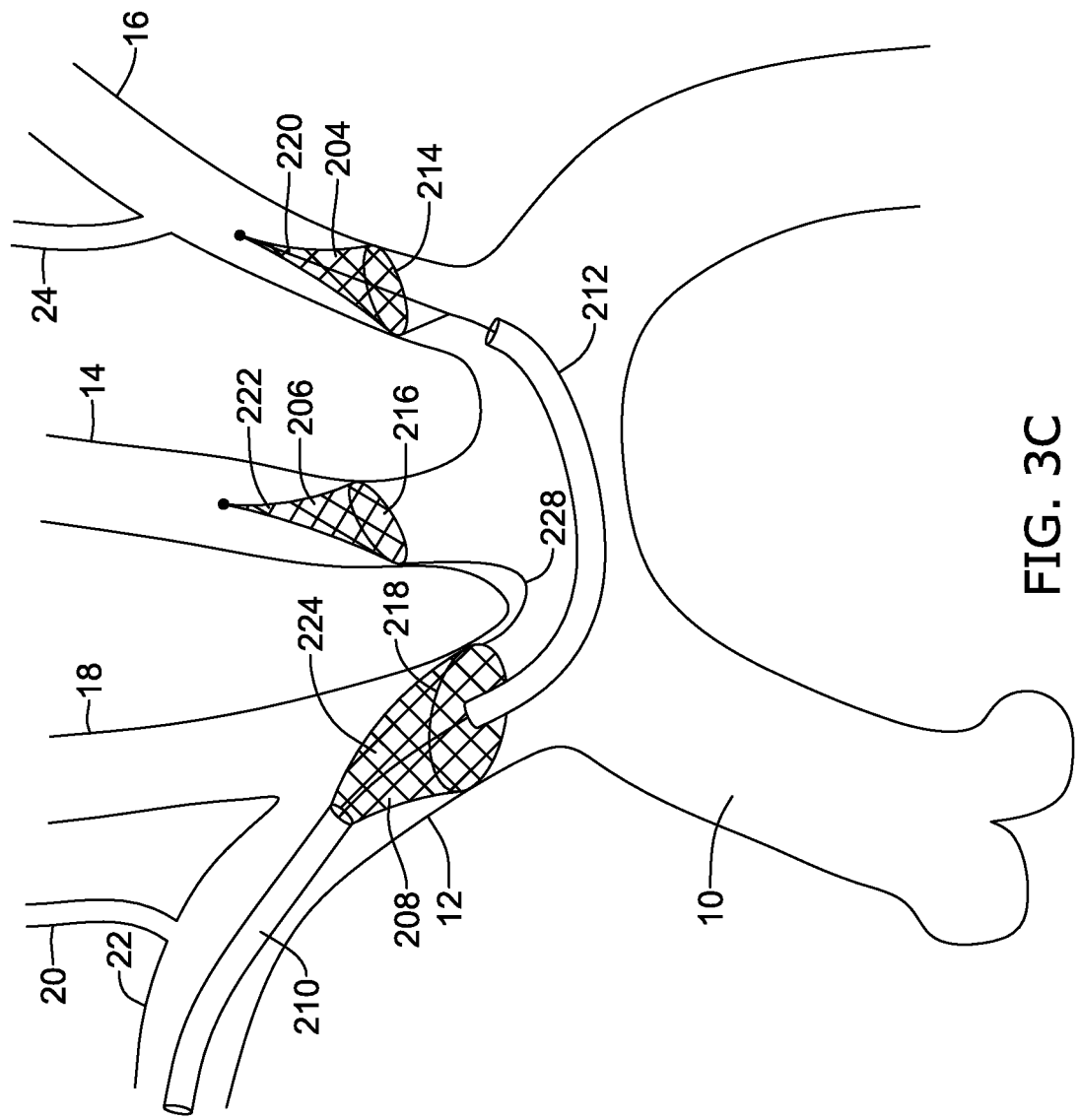

FIGS. 3A-3C illustrate another illustrative protection device, or filter system, 200 in which three filters are delivered with a single delivery device. The filter system 200 may be similar to the second filter system 60 described above. The filter system 200 may include a distal end region 202 including at least a first filter assembly 204 (see, for example, FIG. 3C), a second filter assembly 206, and a third filter assembly 208 (see, for example, FIGS. 3B and 3C and a proximal end region (not explicitly shown) coupled to a handle (not explicitly shown) configured to remain outside the body. The first filter assembly 204, second filter assembly 206, and third filter assembly 208 may each include a support member or frame 214, 216, 218 and a filter element 220, 222, 224 (see, for example, FIG. 3C). The support members 214, 216, 218 may be similar in form and function to the support member 31 described herein. The filter elements 220, 222, 224 may be similar in form and function to the filter element 33 described herein. In some cases, the handle of the filter system 200 may be similar in form and function to the handle 38 described herein. The distal end region 202 may include a proximal sheath 210, a proximal shaft (not explicitly shown) coupled to an expandable proximal, or third, filter assembly 208, a distal shaft 226 coupled to a distal articulatable sheath 212, an intermediate, or second, filter assembly 206, a distal, or first filter assembly 204, and guiding member (not explicitly shown). As can be seen, the filter system 200 may be structurally similar to the second filter system 200 described herein and may be similarly arranged. However, in the filter system 200 illustrated in FIG. 3A, both the second filter assembly 206 and the third filter assembly 208 may be loaded into the proximal sheath 210 for delivery. The second and third filter assemblies 206, 208 may be coupled together via a flexible link 228. In some cases, the flexible link 228 may be made having a predetermined shape to better assist the second filter assembly 206 in cannulation of the left common carotid artery 14. It is contemplated that in some instances, the flexible link 228 may be formed as a dual wire system.

The system 200 is advanced into the subject's right radial artery through an incision in the right arm, or alternatively through the right brachial artery. While not explicitly shown, the system 200 may be advanced over or in conjunction with one or more guidewires. The system is advanced through the right subclavian artery 22 and into the innominate artery 12, and both the distal sheath 212 and a distal portion of the of proximal sheath 210 positioned within the ascending portion of the aorta 10.

The proximal sheath 210 is retracted proximally to allow intermediate filter support element 216 to expand to an expanded configuration within the aorta 10. The system 200 may then be retracted (e.g., proximally displaced) to move the intermediate filter assembly 206 into the left common carotid artery 14, as shown at arrow 230. The predetermined hook shape of the flexible link 228 may help guide the intermediate filter assembly 206 into place. The intermediate support element 216 is moved against the wall of the left common carotid artery 14, as shown in FIG. 3B. The intermediate filter element 222 is also reconfigured into the configuration shown in FIG. 3B. Once expanded, the intermediate filter assembly 206 filters blood traveling through the left common carotid artery 14. In some embodiments, the distal filter assembly 204 and the intermediate filter assembly 206 may be deployed prior to the deployment of the proximal filter assembly 208. The intermediate filter assembly 206 is therefore in position to trap foreign particles and prevent them from traveling into the cerebral vasculature The proximal sheath 210 then be further proximally retracted, as shown at arrow 232, to deploy the proximal filter assembly 208. The position of distal sheath 212 can be substantially maintained while proximal sheath 210 is retracted proximally. The proximal sheath 210 is retracted proximally to allow proximal filter support element 218 to expand to an expanded configuration against the wall of the innominate artery 12, as is shown in FIG. 3B, with the flexible link 228 spanning the distance between the ostium of the left common carotid artery 14 and the innominate artery 12. In some cases, the shape and/or curvature of the flexible link 228 may be manipulated by varying the distance the proximal sheath 210 is retracted. The proximal filter element 224 is secured either directly or indirectly to support element 218 and is therefore reconfigured to the configuration shown in FIG. 3B. Once expanded, the proximal filter assembly 208 filters blood traveling through the innominate artery 12, and therefore filters blood traveling into the right common carotid artery 18 and the right vertebral artery 20. The expanded proximal filter assembly 208 is therefore in position to prevent foreign particles from traveling into the right common carotid artery 18 and the right vertebral artery 20 and into the cerebral vasculature.

The distal sheath 212 is then steered, or bent, and the distal end of the distal sheath 212 is advanced into the left subclavian artery 16. The guiding member (not explicitly shown) is thereafter advanced distally relative to distal sheath 212, allowing the distal support element 214 to expand from a collapsed configuration to a deployed configuration against the wall of the left subclavian artery 16, as shown in FIG. 3C. Alternatively, or additionally, the distal sheath 212 may be proximally retracted to deploy the distal filter assembly 204. The distal filter element 220 is also reconfigured into the configuration shown in FIG. 3C. Once expanded, the distal filter assembly 204 filters blood traveling through the left subclavian artery 16. The expanded distal filter assembly 204 is therefore in positioned to prevent foreign particles from traveling into the left subclavian artery 16 and the left vertebral artery 24 and into the cerebral vasculature. As can be seen in FIG. 3C, the protection system 200 traps foreign particles and prevent them from traveling into the four arteries 14, 18, 20, 24 that carry oxygenated blood to the brain. It is contemplated that when the procedure is completed, the insertion steps may be performed in reverse to remove the system 200.

Figure 4A:
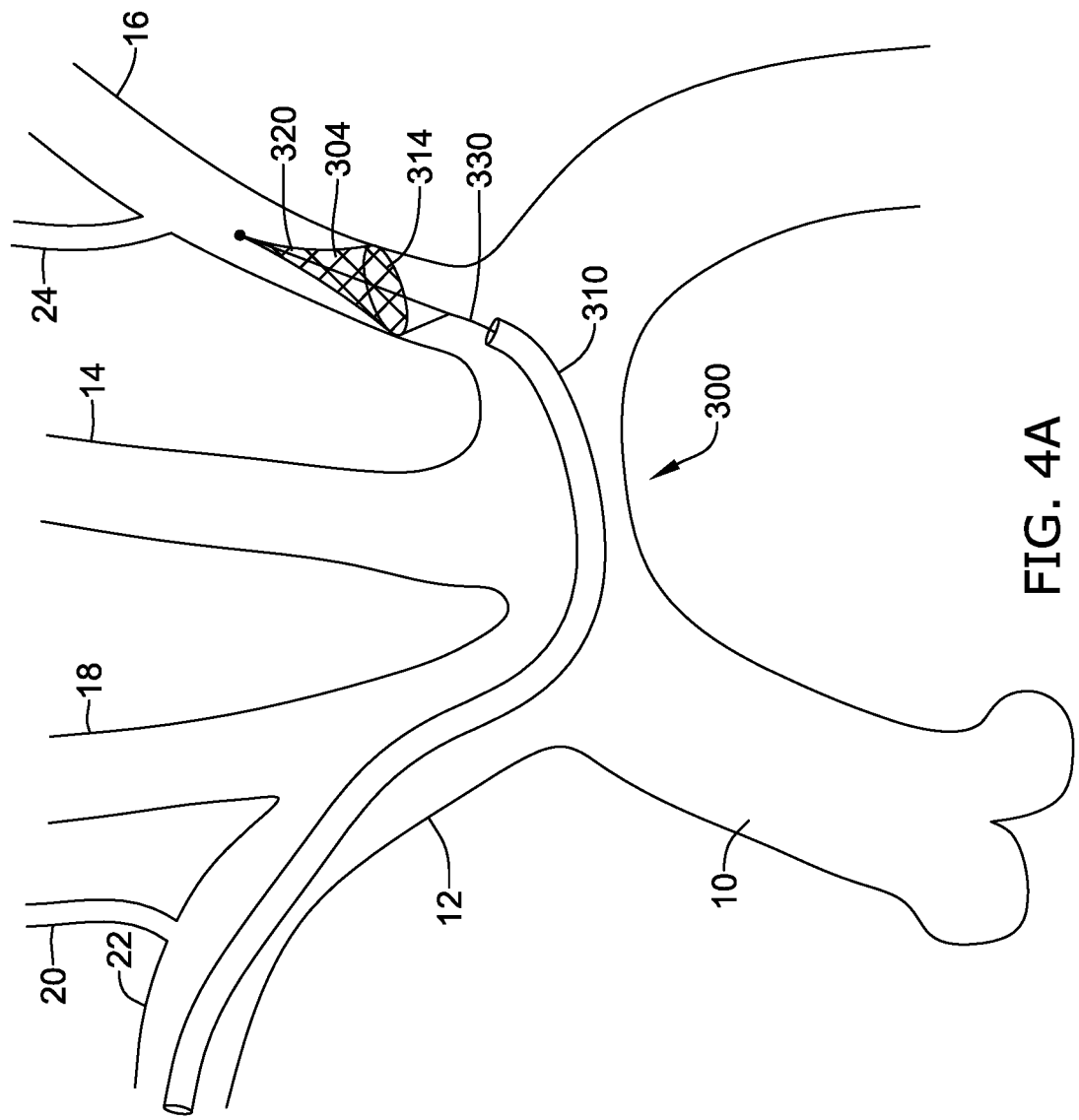
FIGS. 4A-4C illustrate another alternate embodiment of a three filter system.
Figure 4B:
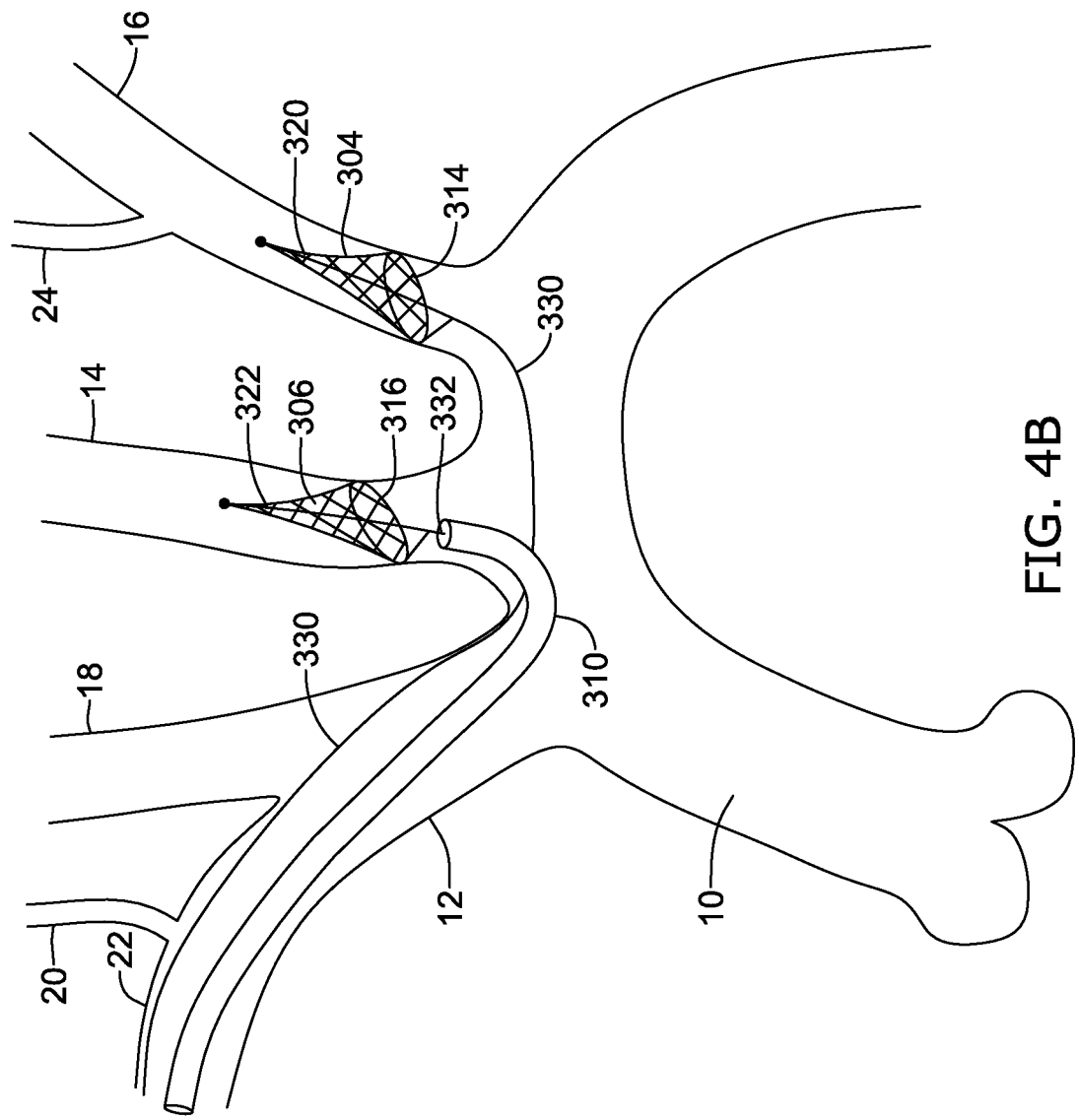
Figure 4C:
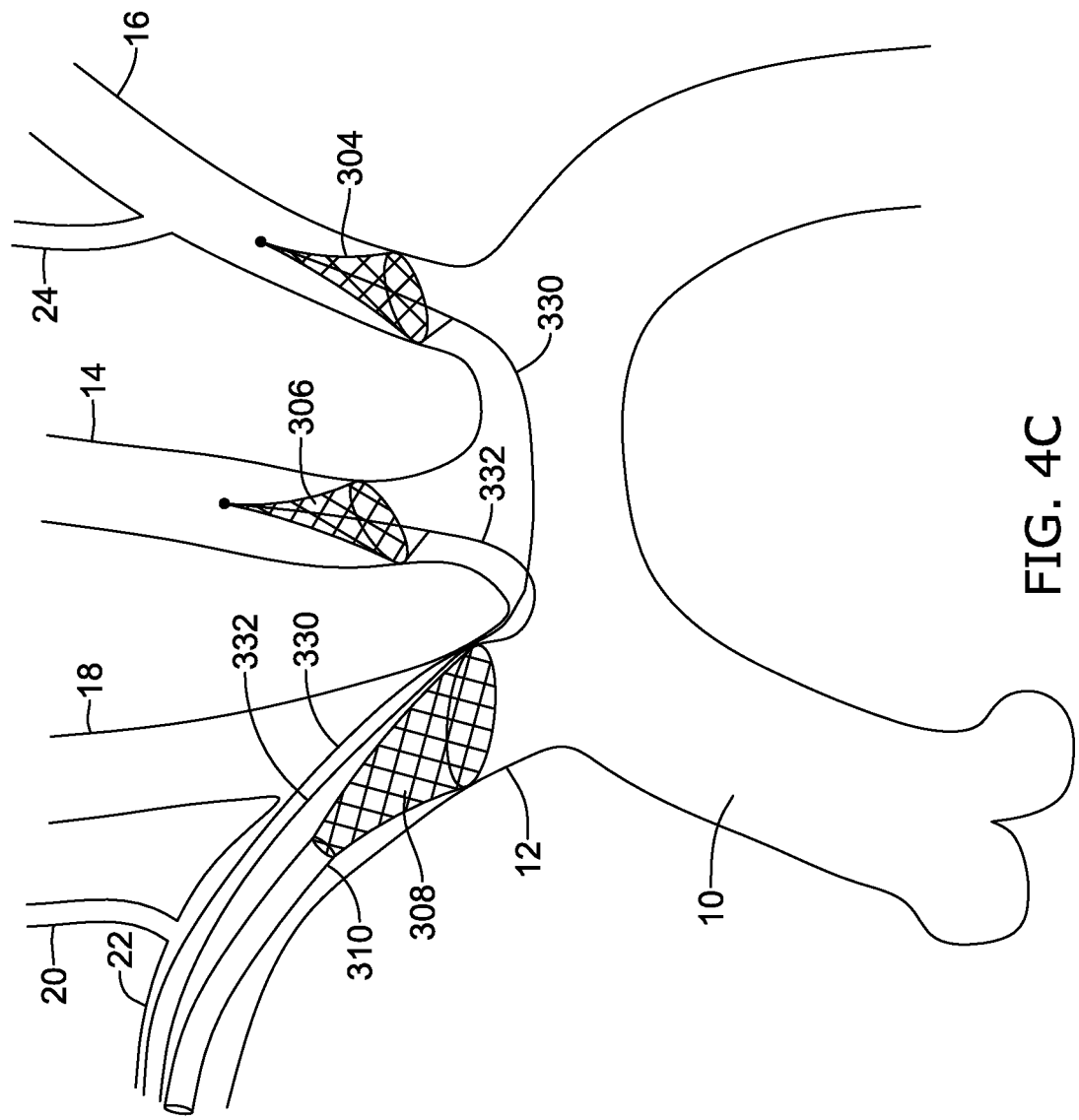

FIGS. 4A-4C illustrate another illustrative protection device, or filter system, 300 in which three filters are delivered separately. The filter system 300 may include steerable sheath 310, a first filter assembly 304, a second filter assembly 306 (see, for example, FIG. 4B, and a third filter assembly 308 (see, for example, FIG. 4C), and a proximal end region (not explicitly shown) coupled to a handle (not explicitly shown) configured to remain outside the body. The first filter assembly 304, second filter assembly 306, and third filter assembly 308 may each include a support member or frame 314, 316, 318 and a filter element 320, 322, 324 (see, for example, FIG. 3C). The support members 314, 316, 318 may be similar in form and function to the support member 31 described herein. The filter elements 320, 322, 324 may be similar in form and function to the filter element 33 described herein. In some cases, the handle of the filter system 300 may be similar in form and function to the handle 38 described herein.

The steerable sheath 310 is advanced into the subject's right radial artery through an incision in the right arm, or alternatively through the right brachial artery. While not explicitly shown, the system 300 may be advanced over or in conjunction with one or more guidewires. The sheath 310 is advanced through the right subclavian artery 22 and into the innominate artery 12, the arch of aorta 10 to a site proximate the ostium of the left subclavian artery 16 (if not actually cannulating left subclavian artery 16). The first filter assembly 304 may then be advanced through a lumen of the sheath 310. Alternately, the first filter assembly 304 may be pre-loaded within the sheath 310 and advanced therewith. The filter assembly 304 may be distally advanced from the sheath 310 (or the sheath 310 proximally retracted) to allow the distal filter support element 314 to expand from a collapsed configuration to a deployed configuration against the wall of the left subclavian artery 16, as shown in FIG. 4A. The distal filter element 320 is also reconfigured into the configuration shown in FIG. 4A. Once expanded, the distal filter assembly 304 filters blood traveling through the left subclavian artery 16. The expanded distal filter assembly 304 is therefore in positioned to prevent foreign particles from traveling into the left subclavian artery 16 and the left vertebral artery 24 and into the cerebral vasculature.

After placement of the first filter assembly 304, the sheath 310 completely withdrawn from the patient such that the filter wire 330 (similar in form and function to filter wire 52b described herein) is free from the sheath 310. The steerable sheath 310 is then advanced into the subject's right radial artery through the incision in the right arm. The sheath 310 is advanced through the right subclavian artery 22 and into the innominate artery 12, the arch of aorta 10 to a site proximate the ostium of the left common carotid artery 14 (if not actually cannulating left common carotid artery 30). The second filter assembly 306 may then be advanced through a lumen of the sheath 310. Alternately, the second filter assembly 306 may be pre-loaded within the sheath 310 and advanced therewith. The filter assembly 306 may be distally advanced from the sheath 310 (or the sheath 310 proximally retracted) to allow the intermediate filter support element 316 to expand from a collapsed configuration to a deployed configuration against the wall of the left common carotid artery 14, as shown in FIG. 4B. The intermediate filter element 322 is also reconfigured into the configuration shown in FIG. 4B. Once expanded, the intermediate filter assembly 306 filters blood traveling through the left common carotid artery 14. The intermediate filter assembly 306 is therefore in position to trap foreign particles and prevent them from traveling into the cerebral vasculature.

After placement of the second filter assembly 306, the sheath 310 is again completely withdrawn from the patient such that a second filter wire 332 (similar in form and function to filter wire 52b described herein) is free from the sheath 310. The steerable sheath 310 is then advanced into the subject's right radial artery through the incision in the right arm. The sheath 310 is advanced through the right subclavian artery 22 and into the innominate artery 12. The third filter assembly 308 may then be advanced through a lumen of the sheath 310. Alternately, the third filter assembly 308 may be pre-loaded within the sheath 310 and advanced therewith. The filter assembly 308 may be distally advanced from the sheath 310 (or the sheath 310 proximally retracted) to allow the proximal filter support element 318 to expand from a collapsed configuration to a deployed configuration against the wall of the innominate artery 12, as shown in FIG. 4C. The proximal filter element 324 is also reconfigured into the configuration shown in FIG. 4C and filters blood traveling through the innominate artery 12, and therefore filters blood traveling into the right common carotid artery 18 and the right vertebral artery 20. The expanded proximal filter assembly 308 is therefore in position to prevent foreign particles from traveling into the right common carotid artery 18 and the right vertebral artery 20 and into the cerebral vasculature. After placement of the third filter assembly 308, the sheath 310 is again completely withdrawn from the patient such that a third filter wire (not explicitly shown) (similar in form and function to filter wire 52b described herein) is free from the sheath 310. As can be seen in FIG. 4C, the protection system 300 traps foreign particles and prevent them from traveling into the four arteries 14, 18, 20, 24 that carry oxygenated blood to the brain. It is contemplated that when the procedure is completed, the insertion steps may be performed in reverse to remove the system 300.

Figure 5:
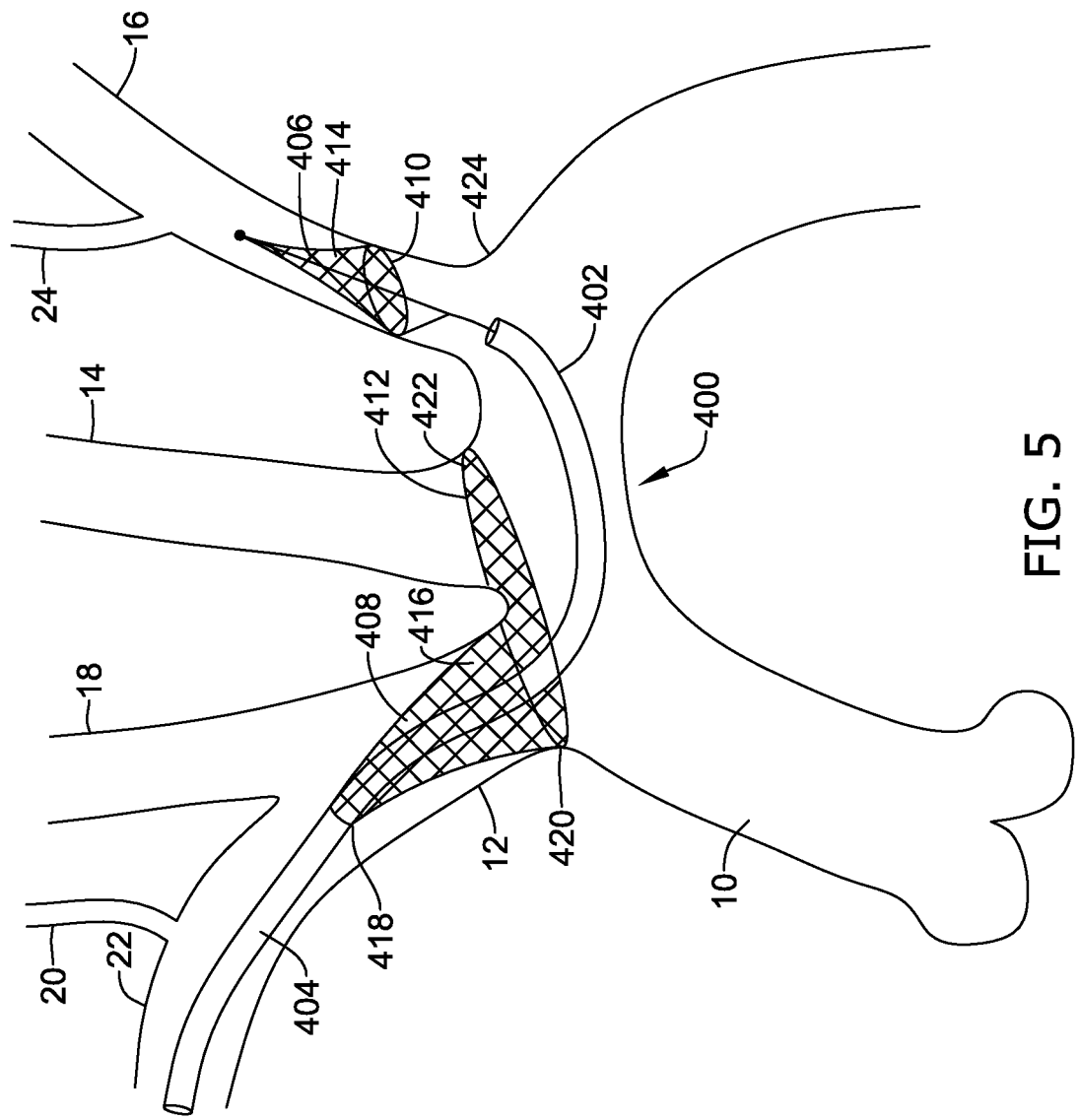
FIG. 5 illustrates an embodiment of a two filter system deployed to fully protect the cerebral apparatus.

FIG. 5 illustrates another illustrative protection device, or filter system 400 in which two filters may be utilized to protect all four arteries 14, 18, 20, 24 that carry oxygenated blood to the brain. The filter system 400 may include an inner sheath 402, an outer sheath 404, a first, or distal, filter assembly 406, a second, or proximal, filter assembly 408, and a proximal end region (not explicitly shown) coupled to a handle (not explicitly shown) configured to remain outside the body. In some embodiments, one or both of the inner sheath 402 and the outer sheath 404 may be steerable. The first filter assembly 406 and the second filter assembly 408 may each include a support member or frame 410, 412 and a filter element 414, 416. The support members 410, 412 may be similar in form and function to the support member 31 described herein. The filter elements 414, 416 may be similar in form and function to the filter element 33 described herein. The second filter assembly 408 may be configured to over the ostium of the both the innominate artery 12 and the left common carotid artery 14. In some cases, the handle of the filter system 400 may be similar in form and function to the handle 38 described herein.

The filter system 400 may be advanced into the subject's right radial (or alternatively, the right brachial) artery through an incision in the right arm. While not explicitly shown, the system 400 may be advanced over or in conjunction with one or more guidewires. The system 400 is advanced through the right subclavian artery 22 and into the innominate artery 12 until the distal end 418 of the outer sheath 404 is adjacent to the ostium 420 of the innominate artery 12. The outer sheath 404 may then be proximally retracted to deploy the proximal filter assembly 408 over the ostia 420, 422 of the innominate and left common carotid arteries 12, 14. As can be seen, the support member 412 and the filter element 416 of the proximal filter assembly 408 may be sized and shaped to extend over both the ostia 420, 422 of the innominate and left common carotid arteries 12, 14. The inner sheath 402 may then be distally advanced toward and, sometimes through, the ostium 424 of the left subclavian artery 16. The inner sheath 402 may be proximally retracted to deploy the distal filter assembly 406 within the left subclavian artery 16. Alternatively, the order in which the filter assemblies 406, 408 are deployed may be reversed. It is contemplated that when the procedure is completed, the insertion steps may be performed in reverse to remove the system 500.

FIG. 6A illustrates another illustrative protection device, or filter system 500 in which a deflector 504, a distal filter assembly 506, and a proximal filter assembly 508 may be utilized to protect all four arteries 14, 18, 20, 24 that carry oxygenated blood to the brain. The filter system 500 may similar in form and function to the filter system 100 described above. The filter system 500 may include a distal end region 502 including at least a deflector 504, a distal filter assembly 506, and a proximal filter assembly 508 and a proximal end region (not explicitly shown) coupled to a handle (not explicitly shown) configured to remain outside the body. The deflector 504, distal filter assembly 506, and proximal filter assembly 508 may each include a support member or frame 514, 516, 518 and a filter element 520, 522, 524. The support members 514, 516, 518 may be similar in form and function to the support member 31 described herein. The filter elements 520, 522, 524 may be similar in form and function to the filter element 33 described herein. However, the deflector 504 may have a generally planar shape such that foreign particulates are not necessarily trapped within the filter element 520 as the deflector is removed. However, the structure of the deflector 504 may be such that blood flow removed any foreign particulates away from the ostium of the left subclavian artery 16 to reduce the likelihood of a foreign particulate entering the left vertebral artery 24. In some cases, the handle of the filter system 500 may be similar in form and function to the handle 38 described herein.

The distal end region 502 may include a proximal sheath 510, a proximal shaft (not explicitly shown) coupled to an expandable proximal filter assembly 508, a distal shaft (not explicitly shown) coupled to a distal articulatable sheath 512, a proximal filter assembly 506, a deflector 504, and guiding member (not explicitly shown). As can be seen, the filter system 500 may be structurally similar to the second filter system 60 and/or the filter system 100 described herein and may be similarly arranged. However, in the filter system 500 illustrated in FIG. 6A, both the deflector 504 and the distal filter assembly 506 may be loaded into the distal sheath 512 for delivery. The deflector and the distal filter assembly 504, 506 may be coupled together via a wire or tether 526. In some cases, the tether 526 may be made have a predetermined shape to better assist the tether 526 in seating and spanning the distance from the ostium of the left subclavian artery 16 to the left common carotid artery 14.

The system 500 is advanced into the subject's right radial artery through an incision in the right arm, or alternatively through the right brachial artery. While not explicitly shown, the system 500 may be advanced over or in conjunction with one or more guidewires. The system is advanced through the right subclavian artery 22 and into the innominate artery 12, and a portion of the system is positioned within aortic arch 10. The proximal sheath 510 is retracted proximally to allow proximal filter support element 518 to expand to an expanded configuration against the wall of the innominate artery 12, as is shown in FIG. 6A. The proximal filter element 524 is secured either directly or indirectly to support element 518 and is therefore reconfigured to the configuration shown in FIG. 6A. The position of distal sheath 512 can be substantially maintained while proximal sheath is retracted proximally. Once expanded, the proximal filter assembly 508 filters blood traveling through the innominate artery 12, and therefore filters blood traveling into the right common carotid artery 18 and the right vertebral artery 20. The expanded proximal filter assembly 508 is therefore in position to prevent foreign particles from traveling into the right common carotid artery 18 and the right vertebral artery 20 and into the cerebral vasculature.

The distal sheath 512 is then steered, or bent, and the distal end of the distal sheath 512 is advanced into the left common carotid artery 14. The guiding member (not explicitly shown) is thereafter advanced distally relative to distal sheath 512, allowing the deflector 504 and the distal filter assembly 506 to be discharged from the distal end of the distal sheath 512. The pre-formed tether 526 may position the deflector proximate the ostium of the left subclavian artery 16 while the distal filter assembly 506 is positioned in the left common carotid artery 14. As the distal filter assembly is deployed, the distal support element 516 expands from a collapsed configuration to a deployed configuration against the wall of the left common carotid artery 14, as shown in FIG. 6A. The distal filter element 522 is also reconfigured into the configuration shown in FIG. 6A. Once expanded, the distal filter assembly 506 filters blood traveling through the left common carotid artery 14. Similarly, the deflector support element 514 expands from a collapsed configuration to a deployed configuration against the wall of the left subclavian artery 16, as shown in FIG. 6A. The deflector filter element 520 is also reconfigured into the configuration shown in FIG. 6A. Once expanded, the deflector 504 filters blood traveling through the left subclavian artery 16. The distal filter assembly 506 is therefore in position to trap foreign particles and prevent them from traveling into the cerebral vasculature and the expanded deflector 504 is in positioned to prevent foreign particles from traveling into the left subclavian artery 16 and the left vertebral artery 24 and into the cerebral vasculature.

It is contemplated that the deflector 504 may not be coupled or linked to the distal filter assembly 506 via the tether 526 (e.g., the tether 526 is not present in the system 500). In such an instance, the deflector 504 may include a deflector wire 528a, 528b. It is contemplated that the deflector is provided with only a single wire 528a or 528b. However, the deflector wire 528a may be positioned outside of the distal sheath 512 (and in some cases, also outside of the proximal sheath 510). In other embodiments, the deflector wire 528b may be disposed within a lumen of the distal sheath 512 and/or the proximal sheath 510.

In some embodiments, the deflector 504 and the distal filter assembly 506 may be deployed prior to the deployment of the proximal filter assembly 508. It is contemplated that when the procedure is completed, the insertion steps may be performed in reverse to remove the system 500. As can be seen in FIG. 6A, the protection system 500 traps foreign particles and prevent them from traveling into the four arteries 14, 18, 20, 24 that carry oxygenated blood to the brain.

Figure 6B:
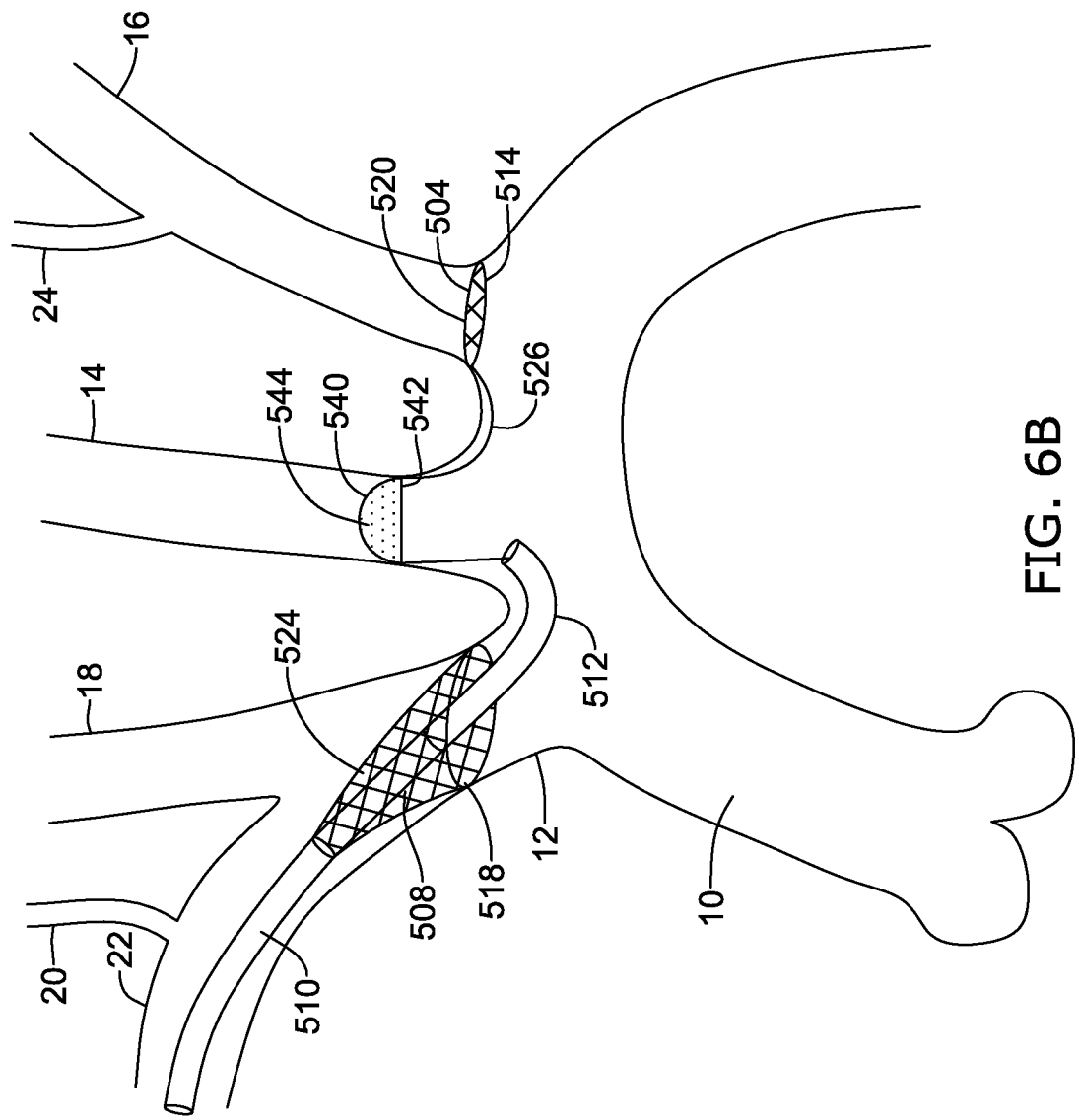

FIG. 6B illustrates an alternative embodiment of the illustrative protection system 500 of FIG. 6A where the distal filter assembly 506 has been replaced with a spring-loaded filter assembly 540. The spring-loaded filter assembly 540 may include a spring-loaded expandable frame 542 and a filter element 544. The spring-loaded expandable frame 542 may have a resiliency or compressibility that allows the spring-loaded filter assembly 540 to be deployed within the aorta 10 and subsequently guided into the left common carotid artery 14. The filter element 544 may be similar in form and function to the filter element 33 described herein.

In the embodiment of FIG. 6B, the system 500 is advanced into the subject's right radial artery through an incision in the right arm, or alternatively through the right brachial artery. While not explicitly shown, the system 500 may be advanced over or in conjunction with one or more guidewires. The system is advanced through the right subclavian artery 22 and into the innominate artery 12, and a portion of the system may positioned within aortic arch 10. The deflector 504 and the spring-loaded filter assembly 540 may be distally advanced from the distal end of the distal sheath 512 in the aorta 10. The articulable distal sheath 512 may then be manipulated to cannulate the left common carotid artery 14 thereby deploying the spring-loaded filter assembly 540 in the left common carotid artery 14 and the deflector 504 across the left subclavian artery 16. The proximal sheath 510 may then be retracted to deploy the proximal filter assembly 508. As can be seen in FIG. 6A, the protection system 500 traps foreign particles and prevent them from traveling into the four arteries 14, 18, 20, 24 that carry oxygenated blood to the brain. It is contemplated that when the procedure is completed, the insertion steps may be performed in reverse to remove the system 500.

Figure 7A:
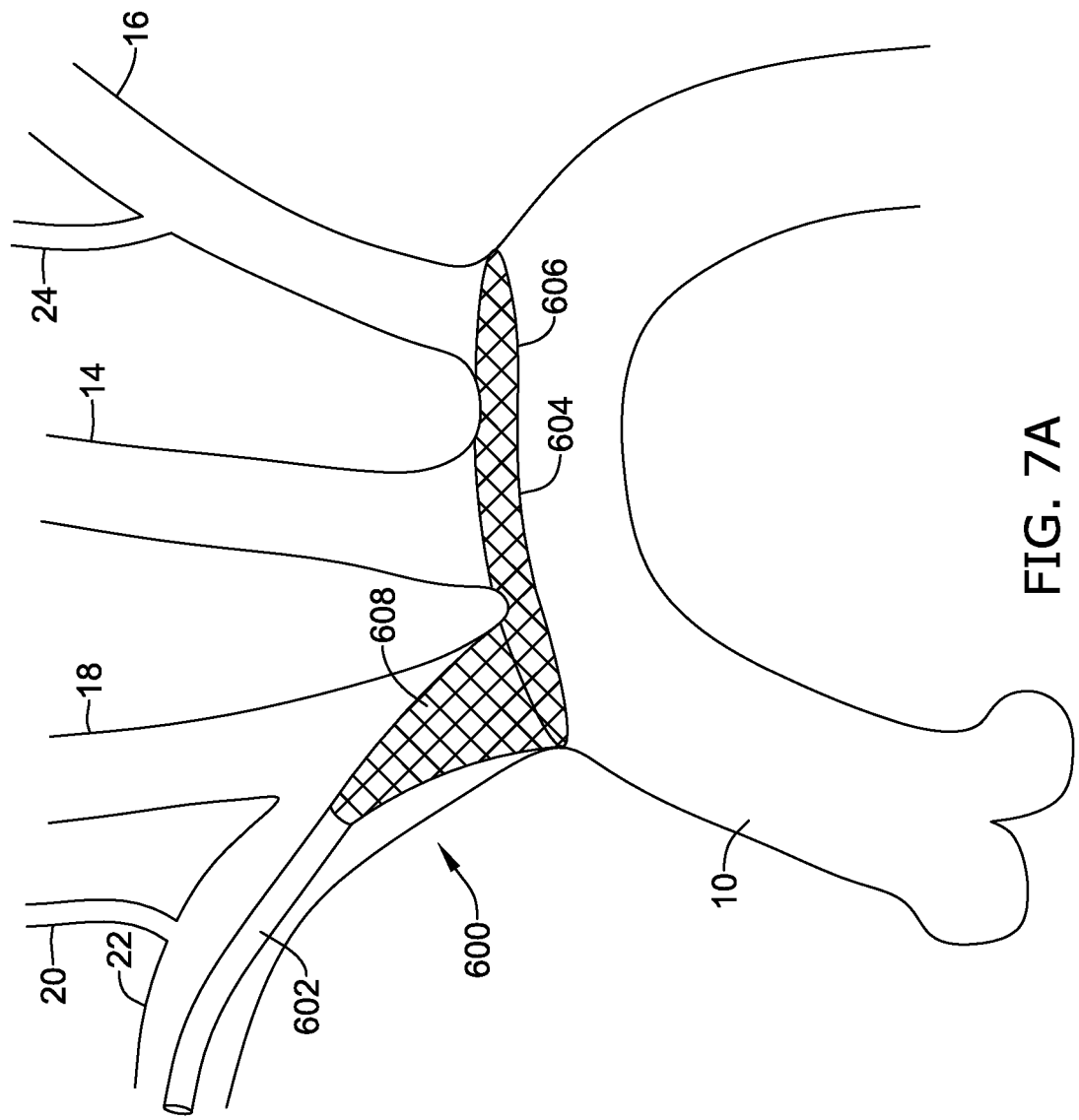
FIGS. 7A-7D illustrate embodiments where only one oversized filter is deployed to protect the cerebral vasculature.
Figure 7B:
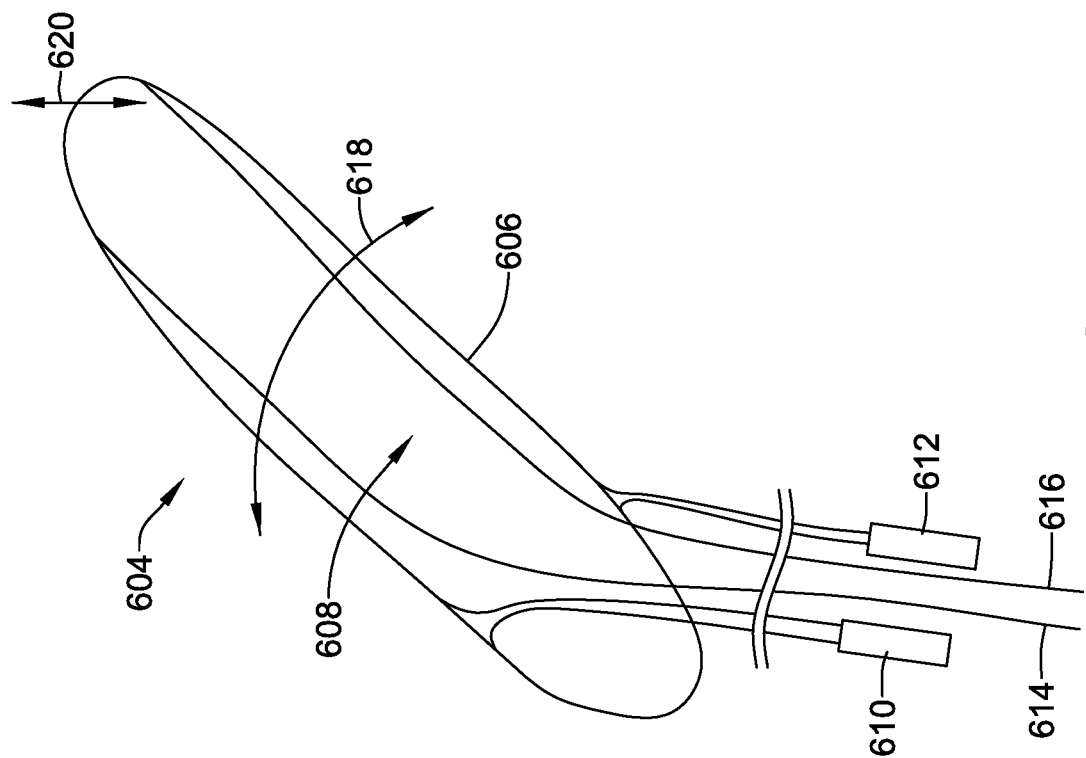

FIG. 7A illustrates another illustrative protection device 600, or filter system in which a single, oversized filter assembly 604 covers the ostia of the left subclavian, left common carotid and innominate arteries 16, 14, 12, which conforming to the curve of the aortic arch 10. Referring additionally to FIG. 7B, which illustrates a schematic view of the filter assembly 604 outside of the body, the filter assembly 604 may include an expandable frame 606 (which may be similar in form and function to the support member 31 described herein), a porous filter material 608 (which may be similar in form and function to the filter element 33 described herein), one or more deployment wires 610, 612 and one or more pull wires 614, 616. The deployment wires 610, 612 may be actuated to exert a force on the frame 606 to shift or bias the filter assembly 604 off axis (shown at arrow 618). The deployment wires 610, 612 may be configured to extend through a lumen of a delivery sheath 602 to a point outside the body where the deployment wires 610, 612 can be manipulated by a user. The pull wires 614, 616 may be actuated to exert a force on the frame 606 to help conform the frame 606 to the upper curve of the aortic arch 10 ((shown at arrow 620). In this manner, not only are all cerebral arteries 14, 18, 20, 24 protected but the filter assembly 604 may not interfere with medical devices, catheters, etc., being passed through the aortic arch 10.

The system 600 is advanced into the subject's right radial artery through an incision in the right arm, or alternatively through the right brachial artery. While not explicitly shown, the system 600 may be advanced over or in conjunction with one or more guidewires. The system is advanced through the right subclavian artery 22 and into the innominate artery 12, and a portion of the system may positioned within aortic arch 10. The filter assembly 604 may be distally advanced from the distal end of the guide sheath 602 and partially into the aorta 10. The deployment wires 610, 612 and/or the pull wires 614, 616 may then be manipulated to position the filter assembly 604 in the desired orientation, such that the filter assembly 604 covers the ostia of the left subclavian, left common carotid and innominate arteries 16, 14, 12. The guide sheath 602 may then be retracted or left within the vasculature during the remainder of the procedure. As can be seen in FIG. 7A, the protection system 600 traps (and/or deflects) foreign particles and prevents them from traveling into the four arteries 14, 18, 20, 24 that carry oxygenated blood to the brain. It is contemplated that when the procedure is completed, the insertion steps may be performed in reverse to remove the system 6

Figure 7C:
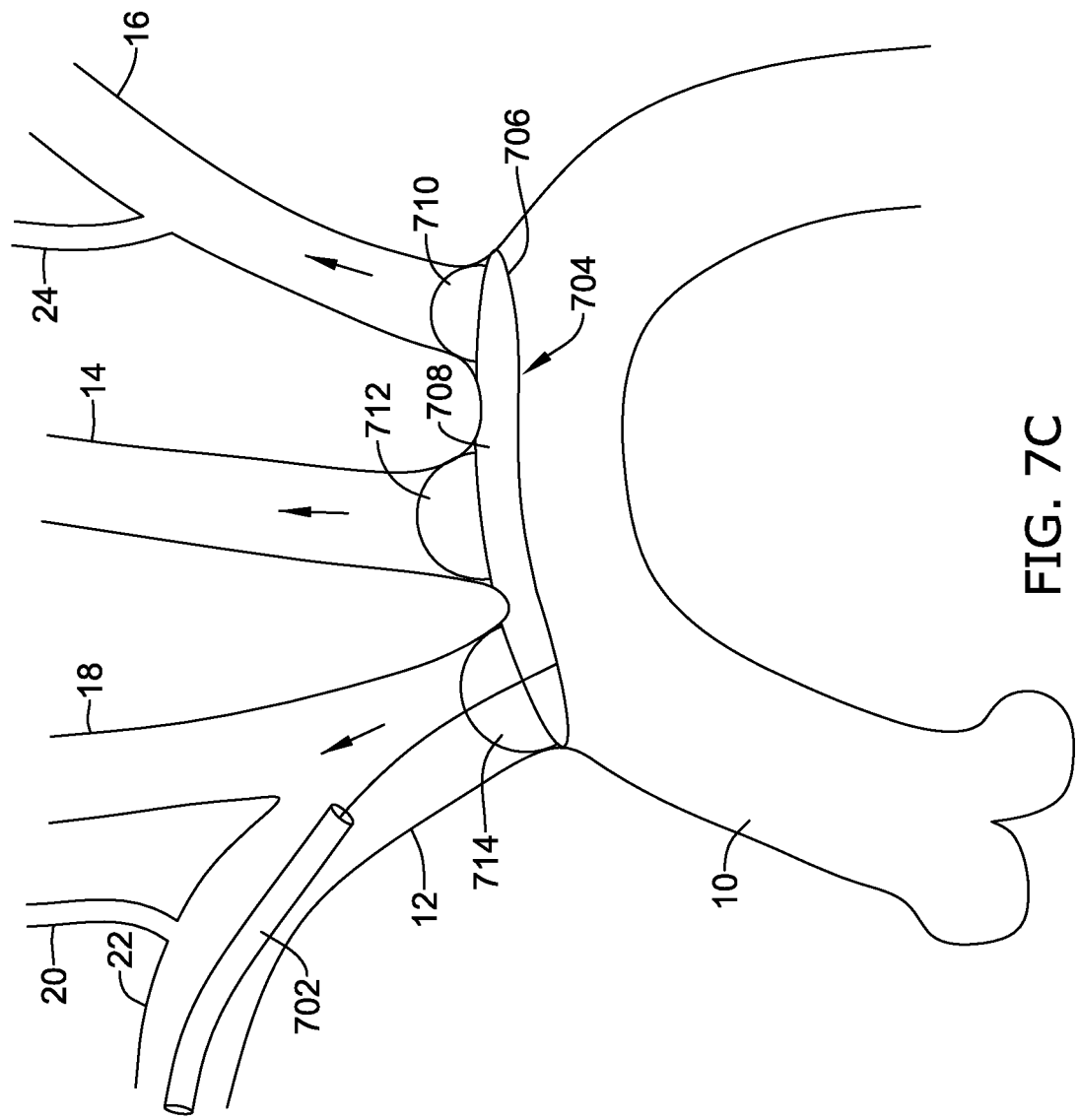
Figure 7D:
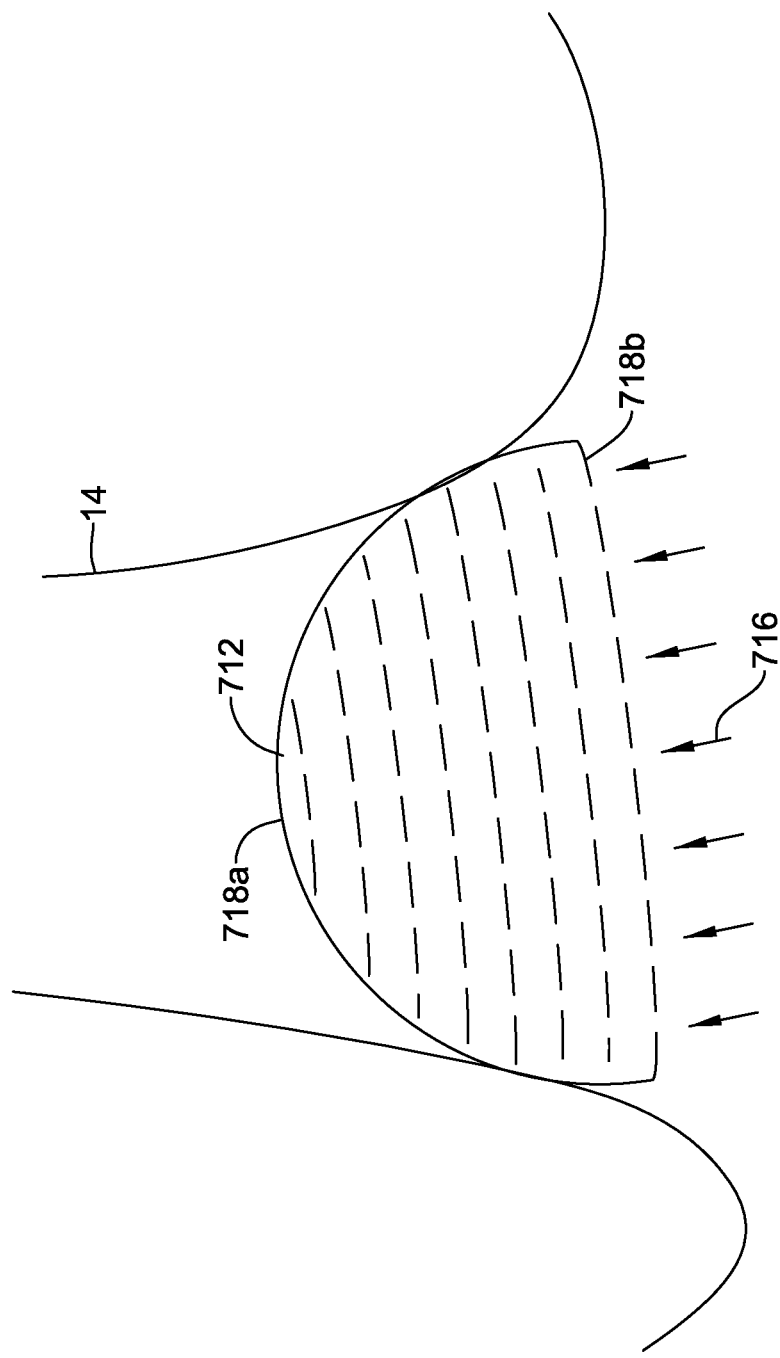

FIG. 7C illustrates another illustrative protection device 700, or filter system in which a single, oversized filter assembly 704 covers the ostia of the left subclavian, left common carotid and innominate arteries 16, 14, 12, which conforming to the curve of the aortic arch 10. The filter assembly 704 may include an expandable frame 706 (which may be similar in form and function to the support member 31 described herein) and a porous filter material 708 (which may be similar in form and function to the filter element 33 described herein). The filter material 708 may include a first shaped section 710, a second shaped section 712, and a third shaped sections 714 configured to prolapse into the left subclavian, left common carotid, and innominate arteries 16, 14, 12, respectively. FIG. 7D illustrates a magnified view of the second shaped section 712. While FIG. 7D is described with respect to the second shaped section 712, the first and third shaped sections 710, 714 may be similarly formed. In some embodiments, the shaped section 712 can be laser drilled, creating holes allowing blood 716 to pass while filtering debris. In some cases, the hole spacing can be denser at the top 718a of the shaped section 712 and become less dense as it nears the end 718b adjacent to the ostia.

However, this is not required. When so provided, the denser holes at the top 718a of the shaped section 712 can cause an increased resistance to blood flow in the area of the shaped section nearer the ostia 718b and, conversely, decreased resistance to blood flow out of the shaped sections 718a where increased flow is needed. The areas, near the ostia, 718b where resistance to flow is increased may create better wall apposition thus reducing risk of debris passing between the membrane 708 and the ostia of the left subclavian, left common carotid and innominate arteries 16, 14, 12. This selective resistance to blood flow may create effective sealing without comprising filtering.

The system 700 is advanced into the subject's right radial artery through an incision in the right arm, or alternatively through the right brachial artery. While not explicitly shown, the system 700 may be advanced over or in conjunction with one or more guidewires. The system is advanced through the right subclavian artery 22 and into the innominate artery 12, and a portion of the system may positioned within aortic arch 10. The filter assembly 704 may be distally advanced from the distal end of the guide sheath 702 and partially into the aorta 10. The filter assembly 704 may be manipulated such that it covers the ostia of the left subclavian, left common carotid and innominate arteries 16, 14, 12. In some cases, the filter assembly 704 may include deployment wires and/or pull wires similar to those described with respect to FIGS. 7A and 7B to facilitate placement of the filter assembly 704. The guide sheath 702 may then be retracted or left within the vasculature during the remainder of the procedure. As can be seen in FIG. 7A, the protection system 700 traps (and/or deflects) foreign particles and prevents them from traveling into the four arteries 14, 18, 20, 24 that carry oxygenated blood to the brain. It is contemplated that when the procedure is completed, the insertion steps may be performed in reverse to remove the system 700.

While the methods and devices described herein may be susceptible to various modifications and alternative forms, specific examples thereof have been shown in the drawings and are described in detail herein. It should be understood, however, that the inventive subject matter is not to be limited to the particular forms or methods disclosed, but, to the contrary, covers all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. In any methods disclosed herein, the acts or operations can be performed in any suitable sequence and are not necessarily limited to any particular disclosed sequence and not be performed in the order recited. Various operations can be described as multiple discrete operations in turn, in a manner that can be helpful in understanding certain embodiments; however, the order of description should not be construed to imply that these operations are order dependent. Additionally, the structures described herein can be embodied as integrated components or as separate components. For purposes of comparing various embodiments, certain aspects and advantages of these embodiments are described. Not necessarily all such aspects or advantages are achieved by any particular embodiment. Thus, for example, embodiments can be carried out in a manner that achieves or optimizes one advantage or group of advantages without necessarily achieving other advantages or groups of advantages. The methods disclosed herein may include certain actions taken by a practitioner; however, the methods can also include any third-party instruction of those actions, either expressly or by implication. For example, actions such as "deploying a self-expanding filter" include "instructing deployment of a self-expanding filter." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 7 mm" includes "7 mm." Phrases preceded by a term such as "substantially" include the recited phrase and should be interpreted based on the circumstances (e.g., as much as reasonably possible under the circumstances). For example, "substantially straight" includes "straight."

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A method of inhibiting embolic material from entering cerebral vasculature, the method comprising:
    positioning a guidewire through a right subclavian artery and into a left subclavian artery;
    tracking a distal portion of a first protection device over the guidewire, the distal portion of the first protection device comprising:
    an outer sheath;
    a first self-expanding filter assembly radially within the outer sheath; and
    at least one of proximally retracting the outer sheath and distally advancing the first self-expanding filter assembly to deploy the first self-expanding filter assembly from the outer sheath in the left subclavian artery upstream of a left vertebral artery;
    after deploying the first self-expanding filter assembly, withdrawing the outer sheath from the right subclavian artery and withdrawing the guidewire into an innominate artery;
    after withdrawing the outer sheath from the right subclavian artery, tracking a distal portion of a second protection device over the guidewire, the distal portion of the second protection device comprising:
    a proximal sheath;
    a proximal self-expanding filter assembly radially within the proximal sheath; a distal sheath; and
    a distal self-expanding filter assembly radially within the distal sheath;
    at least one of proximally retracting the proximal sheath and distally advancing the proximal self-expanding filter assembly to deploy the proximal self-expanding filter assembly from the proximal sheath in the innominate artery;
    steering the distal sheath into a left common carotid artery;
    at least one of proximally retracting the distal sheath and distally advancing the distal self-expanding filter assembly to deploy the distal self-expanding filter assembly from the distal sheath in the left common carotid artery; and
    after deploying the proximal and distal self-expanding filter assemblies, withdrawing the proximal and distal sheaths.

2. The method of claim 1, wherein the first protection device and the second protection device are inserted into a right radial artery or a right brachial artery through a same incision.

3. The method of claim 1, further comprising performing an endovascular procedure, the deployed first, proximal, and distal self-expanding filter assemblies inhibiting embolic material from entering cerebral vasculature through the left vertebral artery, a right common carotid artery, a right vertebral artery and the left common carotid artery during the endovascular procedure.

4. The method of claim 3, further comprising after performing the endovascular procedure, withdrawing the first, proximal, and distal self-expanding filter assemblies.

5. The method of claim 1, wherein the first protection device further comprises an inner member radially inward of the outer sheath.

6. The method of claim 1, further comprising measuring an arterial pressure using one of the first or second protection devices.

7. The method of claim 1, wherein the first protection device further comprises a filter wire coupled to a proximal end of the first self-expanding filter and extending distally therefrom.

8. The method of claim 7, wherein an entirety of a length of the second protection device is tracked over the filter wire.

9. The method of claim 7, wherein less than an entirety of a length of the second protection device is tracked over the filter wire.

10. The method of claim 9, wherein the second protection device further comprises a rapid exchange port.

11. A method of inhibiting embolic material from entering cerebral vasculature, the method comprising:
    positioning a guidewire through a right subclavian artery and into a left subclavian artery;
    tracking a distal portion of a first protection device over the guidewire, the distal portion of the first protection device comprising:
    an outer sheath;
    an inner member radially inward of the outer sheath, the inner member comprising a guidewire lumen; and
    a first self-expanding filter assembly radially between the outer sheath and the inner member, the first self-expanding filter assembly having an opening facing a proximal end of the outer sheath;
    at least one of proximally retracting the outer sheath and distally advancing the first self-expanding filter assembly to deploy the first self-expanding filter assembly from the outer sheath in the left subclavian artery upstream of a left vertebral artery;
    after deploying the first self-expanding filter assembly, withdrawing the outer sheath from the right subclavian artery and withdrawing the guidewire into an innominate artery;
    after withdrawing the outer sheath from the right subclavian artery, tracking a distal portion of a second protection device over the guidewire, the distal portion of the second protection device comprising:
    a proximal sheath;
    a proximal self-expanding filter assembly radially within the proximal sheath; an articulatable distal sheath; and
    a distal self-expanding filter assembly radially within the articulatable distal sheath;

at least one of proximally retracting the proximal sheath and distally advancing the proximal self-expanding filter assembly to deploy the proximal self-expanding filter assembly from the proximal sheath in the innominate artery;

steering the articulatable distal sheath into a left common carotid artery;

at least one of proximally retracting the articulatable distal sheath and distally advancing the distal self-expanding filter assembly to deploy the distal self-expanding filter assembly from the articulatable distal sheath in the left common carotid artery; and after deploying the proximal and distal self-expanding filter assemblies, withdrawing the proximal sheath and the articulatable distal sheath.

12. The method of claim 11, wherein the first protection device and the second protection device are inserted into a right radial artery or a right brachial artery through a same incision.

13. The method of claim 11, further comprising performing an endovascular procedure, the deployed first, proximal, and distal self-expanding filter assemblies inhibiting embolic material from entering cerebral vasculature through the left vertebral artery, a right common carotid artery, a right vertebral artery and the left common carotid artery during the endovascular procedure.

14. The method of claim 13, further comprising after performing the endovascular procedure, withdrawing the first, proximal, and distal self-expanding filter assemblies.

* * * * *